(12) United States Patent
Choi

(10) Patent No.: US 11,783,482 B2
(45) Date of Patent: Oct. 10, 2023

(54) PRODUCING PANORAMIC RADIOGRAPH

(71) Applicants: VATECH Co., Ltd., Gyeonggi-do (KR); VATECH EWOO Holdings Co., Ltd., Gyeonggi-do (KR)

(72) Inventor: Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 0 days.

(21) Appl. No.: 17/828,208

(22) Filed: May 31, 2022

(65) Prior Publication Data

US 2022/0292678 A1 Sep. 15, 2022

Related U.S. Application Data

(62) Division of application No. 15/389,312, filed on Dec. 22, 2016, now Pat. No. 11,373,297.

(30) Foreign Application Priority Data

Oct. 18, 2016 (KR) ......................... 10-2016-0134891
Dec. 16, 2016 (KR) ......................... 10-2016-0172643
Dec. 16, 2016 (KR) ......................... 10-2016-0172677

(51) Int. Cl.
  *G06K 9/00* (2022.01)
  *G06T 7/00* (2017.01)
  (Continued)

(52) U.S. Cl.
  CPC .............. *G06T 7/0012* (2013.01); *A61B 6/14* (2013.01); *A61B 6/463* (2013.01); *G06F 3/0481* (2013.01);
  (Continued)

(58) Field of Classification Search
  CPC ....................................................... A61B 6/14
  See application file for complete search history.

(56) References Cited

U.S. PATENT DOCUMENTS 6,144,501 A    11/2000  Nalwa
7,039,156 B2    5/2006  Arai et al.
(Continued)

FOREIGN PATENT DOCUMENTS

CN    101971614 A    2/2011
CN    101983034 A    3/2011
(Continued)

OTHER PUBLICATIONS

European Patent Office, European Search Report of EP Patent Application No. 17807990.1, dated May 16, 2019.
(Continued)

*Primary Examiner* — Hadi Akhavannik
(74) *Attorney, Agent, or Firm* — IP Legal Services, LLC

(57) ABSTRACT

The disclosure is related to a panoramic radiography device. The panoramic radiography device may include an image processor and a viewer module. The image processor may be configured to produce a primary panoramic image using a first image layer and a secondary panoramic image using a secondary image layer based on a plurality of image frame data, wherein the second image layer is different from the first image layer in at least one of a number, a position, a shape, an angle, and a thickness. The viewer module may be configured to i) provide a graphic user interface having a primary display area and a secondary display area arranged at a predetermined position of the primary display area, ii) display the primary panoramic image at the primary display area, and iii) display a part of the secondary panoramic
(Continued)

image at the secondary display area, wherein the part of the secondary panoramic image corresponds to the predetermined position.

3 Claims, 14 Drawing Sheets

(51) Int. Cl.
G06F 3/0481 (2022.01)
A61B 6/14 (2006.01)
A61B 6/00 (2006.01)
G06T 11/00 (2006.01)
A61B 6/02 (2006.01)

(52) U.S. Cl.
CPC ............ G06T 11/006 (2013.01); A61B 6/027 (2013.01); A61B 6/467 (2013.01); A61B 6/469 (2013.01); A61B 6/5205 (2013.01); A61B 6/5241 (2013.01); G06T 2200/24 (2013.01); G06T 2207/10116 (2013.01); G06T 2207/10124 (2013.01); G06T 2207/30036 (2013.01); G06T 2210/41 (2013.01)

(56) References Cited

U.S. PATENT DOCUMENTS

| | | | |
|---|---|---|---|
| 8,254,520 B2 | 8/2012 | Sadakane et al. | |
| 8,269,818 B2 | 9/2012 | Jones | |
| 8,373,712 B2 | 2/2013 | Lim | |
| 8,433,033 B2 | 4/2013 | Ogawa et al. | |
| 8,634,515 B2 | 1/2014 | Cho et al. | |
| 8,861,679 B2 | 10/2014 | Suuronen et al. | |
| 8,933,929 B1* | 1/2015 | Filip | G06V 10/462 382/154 |
| 10,492,742 B2 | 12/2019 | Nakai et al. | |
| 2004/0066877 A1 | 4/2004 | Arai et al. | |
| 2004/0264753 A1 | 12/2004 | Capolunghi et al. | |
| 2005/0226370 A1 | 10/2005 | Al-Khalidy et al. | |
| 2006/0072848 A1 | 4/2006 | Razzano | |
| 2006/0203959 A1 | 9/2006 | Spartiotis et al. | |
| 2007/0064982 A1 | 3/2007 | Licato et al. | |
| 2007/0237422 A1 | 10/2007 | Zhou et al. | |
| 2008/0019477 A1 | 1/2008 | Spartiotis et al. | |
| 2008/0049894 A1 | 2/2008 | Yasuda et al. | |
| 2008/0063139 A1* | 3/2008 | Pantsar | A61B 6/14 378/40 |
| 2009/0052617 A1 | 2/2009 | Sadakane et al. | |
| 2009/0232274 A1 | 9/2009 | Spartiotis et al. | |
| 2009/0232275 A1 | 9/2009 | Spartiotis et al. | |
| 2009/0310845 A1 | 12/2009 | Ogawa et al. | |
| 2010/0142673 A1 | 6/2010 | Pantsar et al. | |
| 2010/0171810 A1 | 7/2010 | Ohki | |
| 2010/0177865 A1 | 7/2010 | Yoshimura | |
| 2010/0208866 A1 | 8/2010 | Spartiotis et al. | |
| 2010/0246761 A1 | 9/2010 | Pantsar et al. | |
| 2011/0026667 A1 | 2/2011 | Poorter | |
| 2011/0044517 A1* | 2/2011 | Ro | A61B 6/14 382/128 |
| 2011/0305320 A1 | 12/2011 | Suuronen et al. | |
| 2012/0224762 A1 | 9/2012 | Choi et al. | |
| 2012/0230467 A1 | 9/2012 | Katsumata et al. | |
| 2012/0268556 A1 | 10/2012 | Cho et al. | |
| 2013/0003921 A1 | 1/2013 | Spartiotis et al. | |
| 2013/0108011 A1* | 5/2013 | Sadakane | A61B 6/03 378/19 |
| 2013/0300822 A1 | 11/2013 | Mills | |
| 2013/0307923 A1 | 11/2013 | Inglese et al. | |
| 2013/0329854 A1 | 12/2013 | Spartiotis et al. | |
| 2014/0126686 A1 | 5/2014 | Sadakane et al. | |
| 2014/0152562 A1* | 6/2014 | Suzuki | G06F 3/147 345/158 |
| 2014/0254745 A1 | 9/2014 | Nakai et al. | |
| 2014/0340401 A1 | 11/2014 | Graumann et al. | |
| 2015/0004558 A1 | 1/2015 | Inglese et al. | |
| 2015/0117743 A1 | 4/2015 | Choi | |
| 2015/0139524 A1 | 5/2015 | Choi | |
| 2015/0146853 A1 | 5/2015 | Spartiotis et al. | |
| 2015/0305696 A1 | 10/2015 | Yamakawa et al. | |
| 2015/0359504 A1 | 12/2015 | Zhou et al. | |
| 2016/0015332 A1 | 1/2016 | Katsumata et al. | |
| 2016/0095563 A1 | 4/2016 | Fukuda et al. | |
| 2016/0199014 A1 | 7/2016 | Choi et al. | |
| 2016/0310097 A1 | 10/2016 | Bae et al. | |
| 2016/0317107 A1 | 11/2016 | Zhou et al. | |
| 2017/0027536 A1 | 2/2017 | Choi | |
| 2017/0061651 A1 | 3/2017 | Choi | |
| 2017/0258420 A1 | 9/2017 | Inglese et al. | |
| 2017/0281101 A1 | 10/2017 | Choi et al. | |
| 2017/0311910 A1 | 11/2017 | Inglese et al. | |
| 2017/0319160 A1 | 11/2017 | Lu, Ph.D et al. | |
| 2018/0108157 A1 | 4/2018 | Choi | |
| 2018/0325475 A1 | 11/2018 | Choi | |
| 2018/0368673 A1 | 12/2018 | Inglese et al. | |
| 2021/0338180 A1 | 11/2021 | Lu et al. | |

FOREIGN PATENT DOCUMENTS

| | | |
|---|---|---|
| CN | 102469977 A | 5/2012 |
| CN | 103458793 A | 12/2013 |
| CN | 104146768 A | 11/2014 |
| CN | 105411620 A | 3/2016 |
| JP | 2001-333898 A | 12/2001 |
| JP | 2004-313576 A | 11/2004 |
| JP | 2007-136163 A | 6/2007 |
| JP | 2007-236743 A | 9/2007 |
| JP | 3983664 B2 | 9/2007 |
| JP | 2008-086659 A | 4/2008 |
| JP | 2009-531104 A | 9/2009 |
| JP | 2010-011910 A | 1/2010 |
| JP | 2010-178822 A | 8/2010 |
| JP | 2013-116318 A | 6/2013 |
| JP | 2014-094092 A | 5/2014 |
| JP | 2014-514056 A | 6/2014 |
| JP | 2016-007338 A | 1/2016 |
| KR | 10-0917679 B1 | 9/2009 |
| KR | 10-2010-0120815 A | 11/2010 |
| KR | 10-1094180 B1 | 12/2011 |
| KR | 10-2012-0059498 A | 6/2012 |
| KR | 10-1389841 B1 | 4/2014 |
| KR | 10-1664166 B1 | 10/2016 |
| WO | 2012/135190 A2 | 10/2012 |
| WO | 2014/203531 A1 | 12/2014 |
| WO | 2016/043562 A1 | 3/2016 |

OTHER PUBLICATIONS

"Clinical Stomatology: New Advances, New Technologies, New Theories" edited by Yu Li-ying, Fudan University Press, p. 235, Sep. 30, 2008.
The State Intellectual Property Office of People's Republic of China, Office Action of corresponding CN Patent Application No. 201780003187.2, dated Feb. 3, 2021.
Japan Patent Office, Office Action of corresponding JP Patent Application No. 2019-520778, dated Sep. 7, 2021.

* cited by examiner (a)

(b)

PRODUCING PANORAMIC RADIOGRAPH

CROSS REFERENCE TO PRIOR APPLICATIONS

The present application is a Divisional of U.S. patent application Ser. No. 15/389,312 (filed on Dec. 22, 2016), which claims priority under 35 U.S.C. § 119 to Korean Patent Application No. 10-2016-0134891 (filed on Oct. 18, 2016), 10-2016-0172677 (filed on Dec. 16, 2016), and 10-2016-0172643 (filed on Dec. 16, 2016).

The subject matter of this application is related to U.S. patent application Ser. No. 12/863,181 filed on Sep. 20, 2012, U.S. patent application Ser. No. 13/509,042 filed on May 10, 2012, U.S. patent application Ser. No. 14/401,726 filed on Nov. 17, 2014, and U.S. patent application Ser. No. 14/401,716 file on Nov. 17, 2014, the teachings of which are incorporated herein their entity by reference.

BACKGROUND

The present disclosure relates panoramic radiography and, more particularly, to obtaining x-ray image data and producing and providing a dental panoramic radiograph using the obtained x-ray image data.

A medical radiography device is used to produce a radiograph (e.g., x-ray image) of a target object of a patient. For example, a medical radiograph device radiates an x-ray beam to a target object, senses the x-ray beam penetrating the target object using an x-ray sensor, generates electric signals based on the sensed x-ray beam, and produces a radiograph based on the generated electric signals. While the x-ray beam penetrates a target object, the x-ray beam decreases with a different decrement rate according to structures and material on a propagation path. The decreased x-ray beam reaches at the x-ray sensor and is converted into electric signals by photoelectric effacement. The medical radiograph device produces a radiograph using such electric signals reflecting accumulated attenuation generated according to an x-ray beam propagation path. That is, the medical radiograph device provides information on internal structures of a target object as the radiograph (e.g., x-ray image). The medical radiograph device is also referred to as an x-ray imaging machine, an x-ray device, an x-ray machine, and likes.

A computed Tomography (CT) machine provides a CT image and a three-dimensional (3D) radiograph of a target object by reconfiguring x-ray image data. Such a CT machine includes an x-ray generator and an x-ray sensor. The x-ray generator (or, x-ray source) is deployed to face the x-ray sensor, and the target object is positioned between the x-ray generator and the x-ray sensor. The CT machine rotates the x-ray generator and the sensor on the target object and obtains x-ray image data by radiographing the target object in various angles. The CT machine produces a CT image and a 3D x-ray image by reconfiguring or reproducing the obtained x-ray image data.

The three-dimensional (3D) radiograph is frequently used in dental clinics. The 3D radiograph may be referred to a 3D x-ray image. The 3D radiograph is used to examine a dentition for treatments requiring high precision, such as dental implant treatments. Such a 3D radiograph is a tomography produced by a specialized machine such as a 3D computed tomography device (CT), such as a dental 3D CT scanner.

As described, a panoramic x-ray image and a 3D x-ray image are frequently used in dental clinics in order to examine a patient's dentition. Typically, two separated machines are required to obtain the panoramic radiograph and the 3D radiograph.

A panoramic radiograph is a panoramic view of a two-dimensional (2D) x-ray dental arch image including a maxilla dental arch and a mandible dental arch. The panoramic radiograph may be referred to as a panoramic x-ray image. Such a panoramic radiograph shows the maxilla teeth and mandible teeth in a panoramic view. The panoramic radiograph is frequently used by professions in dental clinics for diagnosis of patient's dentition, such as teeth conditions and teeth arrangements. The panoramic radiograph may be produced by radiographing a dental arc by each section and overlapping a plurality of radiographs of each section using a shift and add method which is used in a tomography technology.

Typical radiography has drawbacks. For example, when radiographing a dental arc of a patient, a typical radiography device focuses on a referenced image layer of the dental arc among a plurality of image layers thereof. Such a referenced image layer (e.g., focus region) is decided based on a photographing trajectory of the radiography device. However, such a photographing trajectory is not perfectly matched with an actual dental arc of a patient, for example, an arc of interest. Accordingly, when the photographing trajectory is not matched with the actual dental arc (e.g., arc of interest), it is difficult to get a sharp and clear image of a corresponding dental arc (out of focus).

Due to a tomographic technology property, a panoramic radiograph (e.g., panoramic image) has a spatial resolution in a depth direction according to an x-ray propagation direction. Such a spatial resolution is also referred to as a depth resolution. Such a depth resolution of a panoramic image is in inverse proportion to a width of an image layer in an x-ray radiation direction. That is, the depth resolution of a panoramic image is in inverse proportion to a thickness of an image layer in a vertical direction. A typical panoramic radiography device does not provide tomograms of a region of interest unlike a CT machine. Accordingly, it is difficult to examine some parts of a target object with the panoramic radiograph. For example, it is difficult to identify an inner side root of a molar and an outside root of the same molar with a single panoramic image.

SUMMARY

This summary is provided to introduce a selection of concepts in a simplified form that is further described below in the Detailed Description. This summary is not intended to identify key features or essential features of the claimed subject matter, nor is it intended to be used to limit the scope of the claimed subject matter.

Embodiments of the present disclosure overcome the above disadvantages and other disadvantages not described above. Also, embodiments of the present disclosure are not required to overcome the disadvantages described above, and embodiments of the present disclosure may not overcome any of the problems described above.

In accordance with an aspect of the present embodiment, a panoramic radiograph may be produced using a predetermined number of image layers each having a predetermined thickness, a predetermined angle, and a predetermined shape by enhancing a depth resolution.

In accordance with another aspect of the present embodiment, a primary panoramic radiograph and at least one secondary panoramic radiograph may be produced with different image layers and efficiently displayed together in response to a user input.

In accordance with still another aspect of the present embodiment, a panoramic radiograph of a target object may be produced with multiple secondary panoramic radiographs each having different depth resolution.

In accordance with yet another aspect of the present embodiment, a panoramic radiograph of a target object may be produced with at least one of secondary panoramic radiographs each produced using different image layers of the same target object.

In accordance with still another aspect of the present embodiment, multiple panoramic radiographs of a same target object may be combined and displayed at the same time.

In accordance with at least one embodiment, a panoramic radiography device may be provided. The panoramic radiography device may include an image processor and a viewer module. The image processor may be configured to produce a primary panoramic image using a first image layer and a secondary panoramic image using a secondary image layer based on a plurality of image frame data, wherein the second image layer is different from the first image layer in at least one of a number, a position, a shape, an angle, and a thickness. The viewer module may be configured to i) provide a graphic user interface having a primary display area and a secondary display area arranged at a predetermined position of the primary display area, ii) display the primary panoramic image at the primary display area, and iii) display a part of the secondary panoramic image at the secondary display area, wherein the part of the secondary panoramic image corresponds to the predetermined position.

BRIEF DESCRIPTION OF THE DRAWINGS

The above and/or other aspects of some embodiments of the present invention will become apparent and more readily appreciated from the following description of embodiments, taken in conjunction with the accompanying drawings, of which.

DETAILED DESCRIPTION OF EMBODIMENTS

Figure 1:
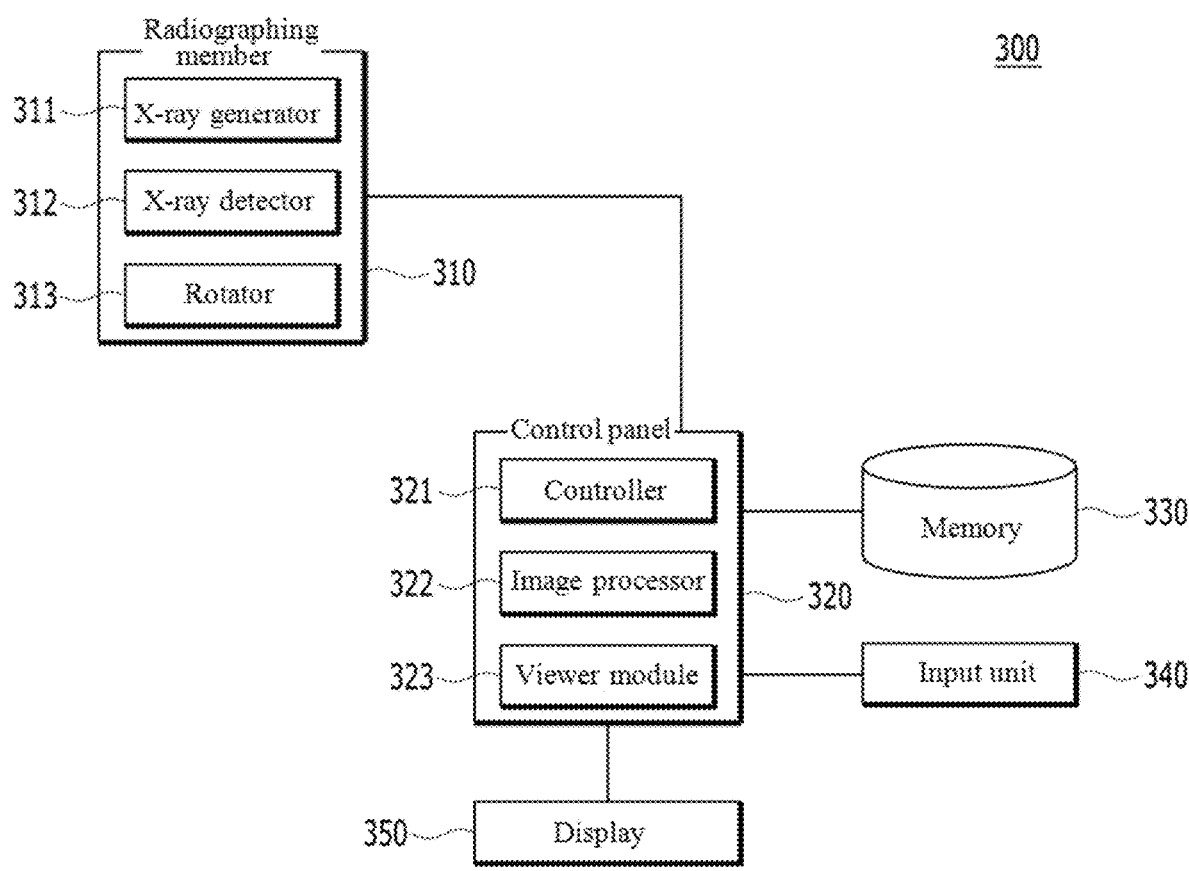
FIG. 1 illustrates a panoramic radiography device in accordance with at least one embodiment of the present disclosure.

Reference will now be made in detail to exemplary embodiments of the present disclosure, examples of which are illustrated in the accompanying drawings, wherein like reference numerals refer to like elements throughout. The embodiments are described below, in order to explain embodiments of the present disclosure by referring to the figures.

In accordance with at least one embodiment, a panoramic radiography device may produce a plurality of panoramic radiographs each produced using different image layers of the same object and combine and display the plurality of panoramic radiographs at the same time. In particular, a panoramic radiography device may produce a primary panoramic radiograph and at least one of secondary panoramic radiographs using different image layers by enhancing a depth resolution and display the produced panoramic radiographs together. For example, panoramic radiography device 300 may i) obtain x-ray image frame data, ii) reconfigure at least one of image layers using x-ray image frame data, iii) produce a primary panoramic radiograph and at least one secondary panoramic radiograph using different image layers, and iv) efficiently display the primary panoramic radiograph and at least one secondary panoramic radiograph together in response to a user input in accordance with at least one embodiment. Hereinafter, such a panoramic radiography device will be described with reference to FIG. 1.

FIG. 1 illustrates a panoramic radiography device in accordance with at least one embodiment of the present disclosure.

Referring to FIG. 1, panoramic radiography device 300 may include radiographing unit 310, control panel 320, memory 330, input unit 340, and display 350. For convenience of description and ease of understanding, panoramic radiography device 300 is illustrated as one computing machine including all the constituent elements 310, 320, 330, 340, and 350. However, embodiments of the present disclosure are not limited thereto. For example, radiographing unit 310 may be separately implemented as an independent machine and connected to control panel 320 through a radio link or a cable. Other constituent elements such as display 350 and memory 330 may be also be separately implemented as an independent machine and connected to control panel 320 through a radio link or a cable.

Radiographing unit 310 may i) radiate an x-ray beam to a target object (e.g., a dental arc of a patient), ii) detect the x-ray beam that penetrated the target object, and iii) obtain data of a plurality of radiographs (e.g., x-ray images) of the target object based on the detected x-ray beam. In order to perform such operation, radiographing unit 310 may include x-ray generator 311, x-ray detector 312, and rotator 313.

X-ray generator 311 may be configured to generate an x-ray beam and radiate the generated x-ray beam toward the target object. X-ray detector 312 may be configured to detect the x-ray beam penetrating through the target object. X-ray detector 312 may be referred to as an x-ray sensor. Rotator 313 may be configured to rotate x-ray generator 311 and x-ray detector 312 on a target object.

In particular, radiographing member 310 may perform a scanning sequence operation for obtaining x-ray image data. That is, upon initiation of the scanning sequence operation, radiographing member 310 may rotate x-ray generator 311 and x-ray detector 312 on a target object (e.g., dental arc of a patient). Radiographing member 310 may move a rotation axis of rotating x-ray generator 311 and x-ray detector 312 in one dimension and/or two dimensions.

During the scanning sequence operation, x-ray generator 311 may radiate x-ray beam at various positions and angles toward x-ray detector 312 through the target object. X-ray detector 312 may receive the x-ray beam, radiated from x-ray generator 311 and penetrating through the target object, and generate data of a plurality of x-ray images of the target object, which is also referred to as a plurality of frame data. Such a scanning sequence operation will be described in more detail with reference to FIG. 2.

Control panel 320 may include controller 321, image processor 322 and viewer module 323. Controller 321 may be configured to control rotating x-ray generator 311 and x-ray detector 312. Controller 321 may include a central processing unit configured to control constituent elements such as image processor 322, viewer module 323, memory 330, input unit 340, and display 350. Controller 320 may be connected to radiographing member 310 wirelessly and through a wire (e.g., cable).

Control panel 320 may receive data of a plurality of x-ray image frames (e.g., x-ray image frame data) from radiographing member 310 and store the obtained x-ray image frame data in memory 330. Image processor 322 may perform a panoramic radiograph producing operation in accordance with at least one embodiment. Image processor 322 may reconfigure at least one image layer based on the stored x-ray image frame data and produce at least one x-ray panoramic image using the reconfigured at least one image layer. The image layer may be a predetermined focused region in a dental arc. Viewer module 323 may display the produced x-ray panoramic images. Control panel 320 may store the produced x-ray panoramic image in memory 330. Although it is not shown in FIG. 1, control panel 320, memory 330, input unit 340 and display 350 may be implemented as at least one independent computing device and associated peripheral devices.

Control panel 320 may include a central processing unit for controlling general operations of constituent elements of panoramic radiography device 300. For example, control panel 320 may be implemented using at least one of application specific integrated circuits (ASICs), digital signal processors (DSPs), digital signal processing devices (DSPDs), programmable logic devices (PLDs), Field-programmable gate arrays (FPGAs), processors, controllers, micro-controllers, and microprocessors. Control panel 320 may be implemented as firmware and/or software module, which may be executable on a hardware platform. In this case, such a firmware or a software module may be implemented by at least one of software applications written in a predetermined programming language.

Figure 4:
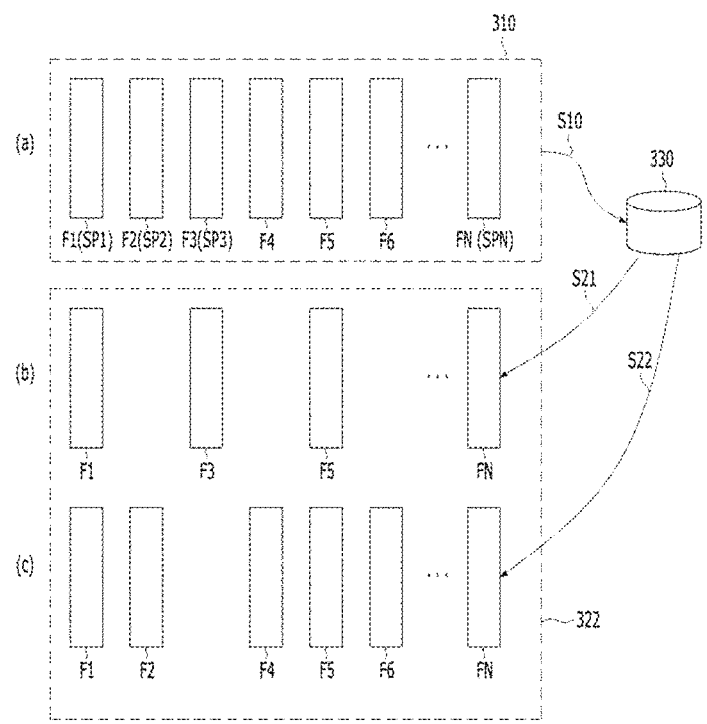
FIG. 4 illustrates obtaining data of a plurality of x-ray image frame as a result of a scanning sequence operation in accordance with at least one embodiment.

Viewer module 323 may perform operations for displaying x-ray panoramic images reconfigured and produced by image processor 322. Such viewer module 323 may perform operations for producing a graphic user interface in a predetermined format according to a pre-stored algorithm and properly displaying the graphic user interface with an x-ray panoramic image reconfigured and produced by image processor 322. Furthermore, viewer module 323 may perform operations for providing control options (e.g., menus) to a user through the graphic user interface in order to enable the user to control the displayed panoramic images (e.g., such as resizing, copying, switching related panoramic images). In addition, view module 323 may perform operations for providing various indicators to help the user to recognize information on the displayed panoramic images. Such graphic user interfaces, options, and indicators will be described with reference to the accompanying drawings such as FIG. 5, FIG. 14, and FIG. 15 to FIG. 20. For example, FIG. 4 illustrates such a graphic user interface with an x-ray panoramic image displayed on display 350. Viewer module 323 may be implemented by at least one of firmware and/or software module. Viewer module 323 may be included as a part of image processor 322.

Memory 330 may store various types of information, generated in panoramic radiography device 300 and received from other entities. Memory 330 may further store various types of applications and software programs for controlling constituent elements or performing operations associated with producing panoramic radiograph.

In accordance with at least one embodiment, memory 330 may store intermediate image data generated for producing a panoramic radiograph, resultant image data, information and variables necessary to perform operations for producing the panoramic radiograph. For example, memory 330 may store various types of image data, such as image data in a digital imaging and communications in medicine (DICOM) type, a BMP type, a JPEG type, and a TIFF type. Furthermore, memory 330 may store i) data of a plurality of x-ray image frames obtained during the scanning sequence operation, ii) image layers reconfigured based on the x-ray image frame data, and iii) panoramic radiographs (e.g., panoramic x-ray images) produced using the image layers in accordance with at least one embodiment.

Memory 330 may further store software programs and a firmware. Memory 330 may include a flash memory, a hard disk, a multimedia card (MMC), a secure digital card, an extreme digital card, a random access memory (RAM), a static random access memory (SRAM), a read-only memory (ROM), an electrically erasable programmable read-only memory (EEPROM), a programmable read-only memory, a magnetic resistive random access memory, a magnetic disk, and an optical disk. However, the embodiments of the present disclosure are not limited thereto.

Input unit 340 may receive various types of signals from an operator for controlling panoramic radiography device 300 in accordance with at least one embodiment. Input unit 340 may include a keyboard, a keypad, a touch pad, a mouse, and likes. In addition, input unit 340 may be a graphic user interface capable of detecting a touch input.

Furthermore, Input unit 340 may provide an interface for receiving input information from other entities including an operator. Such input unit 340 may be realized to support in various types of standardized protocols and interface schemes. In addition, input unit 340 may be referred to as an input circuit.

Display 350 may be a device for displaying a graphic unit interface and at least one panoramic radiograph (e.g., primary panoramic radiograph with at least one secondary panoramic radiograph) produced by panoramic radiography device 300. Display 350 may be various types of a display device, such as a liquid crystal display (LCD), a light emitting diode (LED) display, an active matrix organic light emitting diode (AMOLED) display, a cathode ray tube (CRT) display, and likes. Further, display 350 may be a touch screen for receiving a touch input from a user.

In accordance with at least one embodiment, panoramic radiography device 300 may further include a communication circuit. The communication circuit may be a circuit for communicating with other entities coupled to panoramic radiography device 300. Such a communication circuit may enable panoramic radiography device 300 to communicate with other entities through a communication network. For example, the communication circuit 300 may establish at least one of wireless and wired communication links to other entities (e.g., a 3D CT scanner and a display) through a communication network or directly. Through the established communication links, the communication circuit may receive information from or transmit information to a 3D CT scanner and a display. In FIG. 1, panoramic radiography device 300 is illustrated as including radiographing member 310, but embodiments are not limited thereto. For example, panoramic radiography device 300 may not include radiographing member 310 and receive data of a plurality of x-ray image frames from other entities (e.g., 3D CT scanner) through the communication circuit.

Furthermore, the communication circuitry may transmit and receive signals to/from other entities through a communication network based on various types of communication schemes. The communication circuitry may be referred to as a transceiver and include at least one of a mobile communication circuit, a wireless internet circuit, a near field communication (NFC) circuit, a global positioning signal receiving circuit, and so forth. Particularly, the communication circuit may include a short distance communication circuit for short distance communication, such as NFC, and a mobile communication circuit for long range communication through a mobile communication network, such as long term evolution (LTE) communication or wireless data communication (e.g., WiFi). In addition, the communication circuit may provide a communication interface between panoramic radiography device 300 and other entities using various communication schemes.

In accordance with another embodiment, panoramic radiography device 300 may be implemented without radiographing member 310 and display 350. In this case, panoramic radiography device 300 may be connected to at least one of a panoramic x-ray device and a 3D CT scanner and a standalone display. The panoramic x-ray device or the 3D CT scanner may produce data of a plurality of x-ray image frames of a target object and provide the x-ray image frame data to panoramic radiography device 300. Display 350 may receive a primary panoramic radiograph with at least one secondary panoramic radiographs produced by panoramic radiography device 300 and display the received panoramic radiographs with a predetermined graphic user interface in response to an operator's control. For example, the panoramic x-ray device and the 3D CT scanner may be a typical 3D radiography machine such as a cone beam computed tomography (CBCT) and a computed tomography (CT).

In accordance with still another embodiment, panoramic radiography device 300 may be implemented as a circuit board attachable to or detachable from a predetermined slot in a circuit board. In this case, such panoramic radiography device 300 may be inserted at a predetermined slot of other entities such as a typical 3D CT scanner. In this case, panoramic radiography device 300 may use constituent elements (e.g., processors or memoires) of the typical 3D CT scanner for producing a panoramic radiograph. Furthermore, panoramic radiography device 300 may be implemented as a circuitry card with a predetermined communication interface such as a universal serial bus (USB) interface. Such panoramic radiography device 300 may be coupled with other entities such as a typical 3D CT scanner through a USB slot. In this case, panoramic radiography device 300 may use constituent elements (e.g., processors or memoires) of the typical 3D CT scanner for producing a panoramic radiograph. Furthermore, panoramic radiography device 300 may be implemented as software program or application and installed in other entities. In this case, upon installing and execution of the predetermined software program, the other entities might produce a panoramic radiograph by controlling constitute elements of the other entities As another example, panoramic radiography device 300 may be located a comparatively long distance from a source entity of x-ray image frame data. In this case, panoramic radiography device 300 may be connected to the source entity through a communication network. As still another example, panoramic radiography device 300 may be not coupled to the source entity. In this case, panoramic radiography device 300 may obtain x-ray image frame data of a target object i) by downloading from other entities coupled through a communication network, ii) from a secondary external memory coupled thereto through a predetermined interface, iii) inputted by an operator through an input circuit of panoramic radiography device 300. However, embodiments of the present disclosure are not limited thereto.

As described, panoramic radiography device 300 may i) obtain x-ray image frame data, ii) reconfigure at least one of image layers using x-ray image frame data, iii) produce a primary panoramic radiograph and at least one secondary panoramic radiograph using different image layers, and iv) efficiently display the primary panoramic radiograph and at least one secondary panoramic radiograph together in response to a user input in accordance with at least one embodiment.

In accordance with at least one embodiment, a primary panoramic image may be produced based on at least one first image layer, and at least one secondary panoramic image be produced based on at least one second image layer which is partially or entirely different from the first image layer. Furthermore, panoramic images may be produced to have a high depth resolution which is significantly improved as compared to a typical panoramic image. Hereinafter, operations of panoramic radiography device 200 that will be described in more detail with reference to the accompanying drawings.

Figure 2:
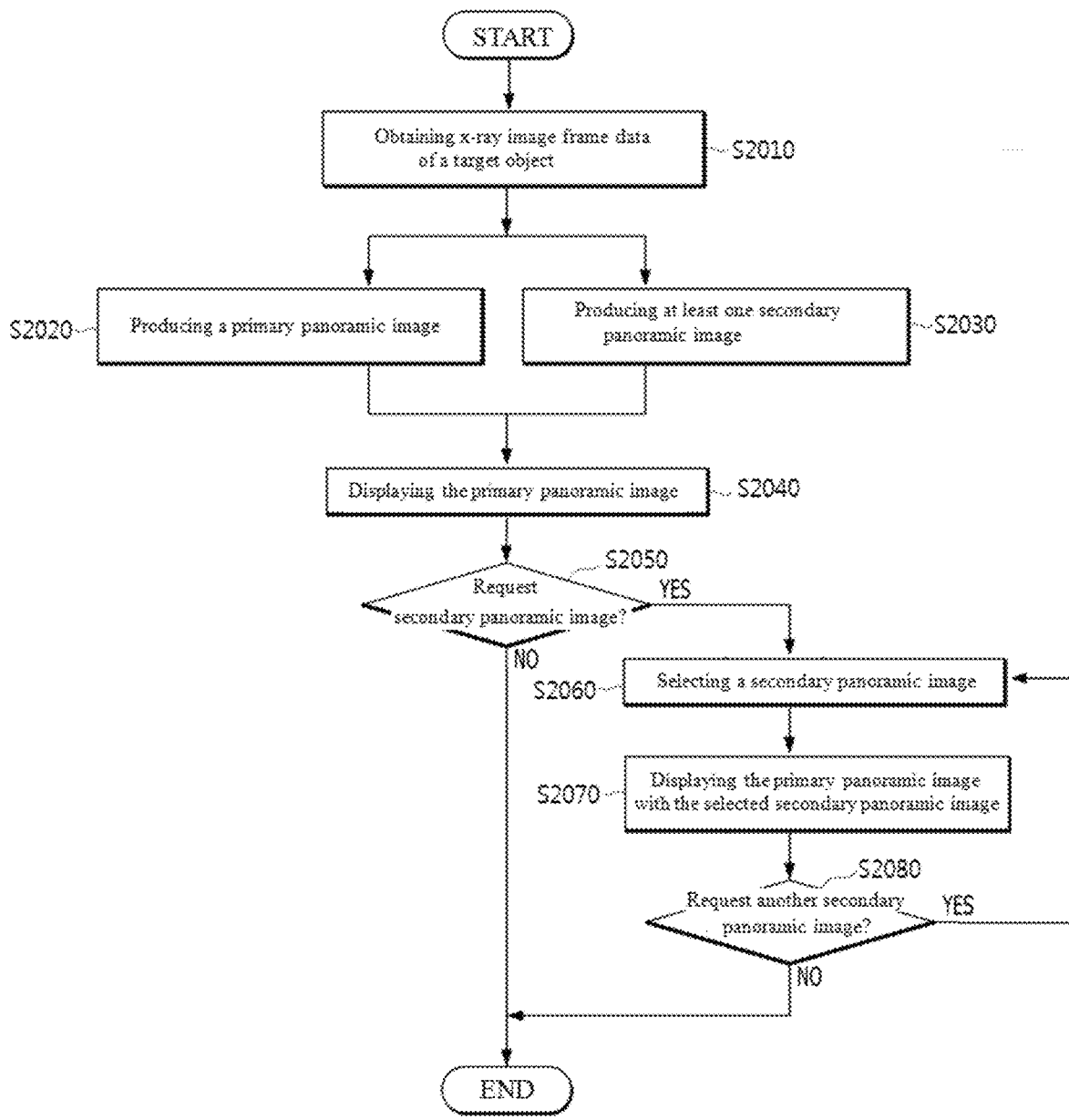
FIG. 2 is a flowchart for describing operations of a panoramic radiograph device in accordance with at least one embodiment.

FIG. 2 is a flowchart for describing operations of a panoramic radiograph device in accordance with at least one embodiment. In particular, the flowchart of FIG. 2 illustrates a method for producing a primary panoramic radiograph and at least one of secondary panoramic radiograph and efficiently displaying the produced radiographs together in accordance with at least one embodiment.

Referring to FIG. 2, operations of panoramic radiograph device 300 may include a scanning sequence operation, a primary panoramic image producing operation, a secondary panoramic image producing operation, and a panoramic image displaying operation in overall. That is, the method of producing and displaying panoramic radiographs may include obtaining x-ray image frame data of a target object as a result of performing a scanning sequence operation at step S2010, producing a primary panoramic image at step S2020, producing at least one secondary panoramic image at step S2030, and displaying the primary panoramic image with at least one secondary panoramic image at step S2040 to S2080. In particular, at steps S2050 to S2080, at least one secondary panoramic image may be selected by a user and displayed with the primary panoramic image layer. Such operations related to steps S2050 to S2080 will be described with reference to FIG. 15, FIG. 18, and FIG. 19. Hereinafter, each operation of panoramic radiograph device 300 will be described in detail.

Figure 3:
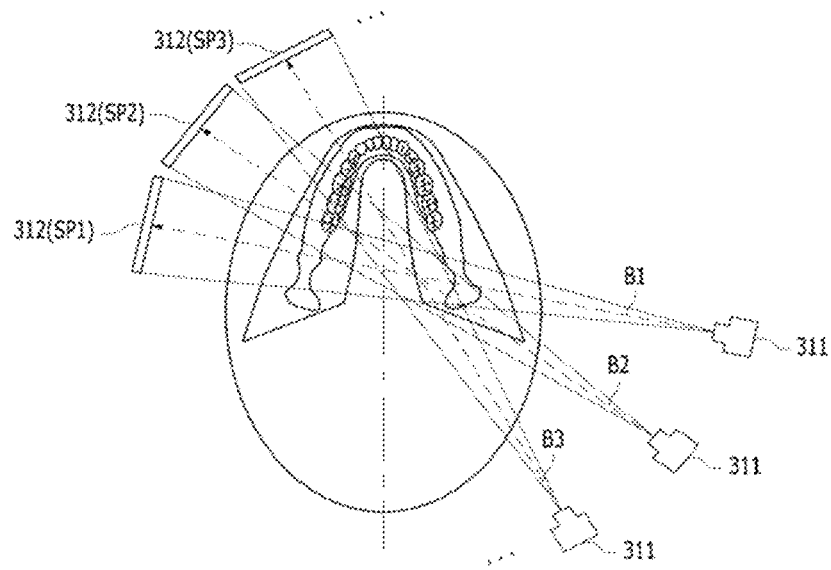
FIG. 3 is a diagram for describing a scanning sequence operation of a panoramic radiography device in accordance with at least one embodiment.

FIG. 3 is a diagram for describing a scanning sequence operation of a panoramic radiography device in accordance with at least one embodiment.

Referring to FIG. 3, panoramic radiography device 300 may perform a scanning sequence operation for obtaining data of a plurality of x-ray image frames of a target object (e.g., a dental arc of a patient) in accordance with at least one embodiment. In the scanning sequence operation, panoramic radiography device 300 may sequentially rotate radiographing member 310 along a predetermined radiographing trajectory and obtain data of a plurality of x-ray image frames while sequentially rotating radiographing member 310.

For example, in response to a user input, panoramic radiography device 300 may rotate x-ray generator 311 and x-ray detector 312 around a dental arc of a patient with x-ray generator 311 facing x-ray detector 312. During the rotation, x-ray generator 311 radiates x-ray beams toward x-ray detector 312 through the target object (e.g., dental arc) at a predetermined interval. For example, x-ray generator 311 radiates x-ray beams B1, B2, B3, and x-ray detector 312 receives, at positions SP1, SP2, SP3, the x-ray beams that penetrated the target objects. That is, x-ray detector 312 receives x-ray beams B1, B2, and B3 penetrating the dental arc in various positions and angles and generate x-ray image frame data based on the received beams. The x-ray image frame data may be also referred to x-ray image data, x-ray frame data, or frame data.

A plurality of x-ray image frame data are sequentially obtained by a frame unit of x-ray detector 312. Using the obtained x-ray image frame data, panoramic images may be produced using a plurality of image layers. That is, a plurality of image layers of the target object may be reconfigured using the obtained x-ray image frame data, and panoramic images including a primary panoramic image and at least one secondary panoramic image may be produced using the image layers. Such a technique is disclosed in U.S. patent application Ser. No. 12/863,181, which is filled in U.S. by a common applicant. The subject matter of this application is related to U.S. patent application Ser. No. 12/863,181, the teaching of which are incorporated herein their entirety by reference.

In at least one embodiment of the present disclosure, x-ray detector 312 has a width comparatively wider than a typical panoramic photography device. The width is a width in a rotation direction of the x-ray detector 312. For example, in general, a width of a typical x-ray detector is about 6 mm. Unlike the typical x-ray detector, the width of x-ray detector 312 is in between about 4 cm and about 6 cm. Although x-ray detector 312 having a comparative wide width is used, panoramic radiography device 300 in accordance with at least one embodiment obtains sufficient data for reconfiguring and producing panoramic images with improved depth resolution. Because of comparatively wide x-ray detector 312, panoramic radiography device 300 requires a comparatively short x-ray radiation time and a comparatively less x-ray radiation amount although a radiographing trajectory thereof is same.

FIG. 4 illustrates obtaining data of a plurality of x-ray image frame as a result of a scanning sequence operation in accordance with at least one embodiment.

Referring to FIG. 4, a diagram (a) illustrates an operation for obtaining data for a plurality of x-ray image frames as result of a scanning sequence operation. For example, at step S10, radiographing member 310 performs a scanning sequence operation and obtains data for a plurality of x-ray image frames F1, F2, F3 . . . FN (SPN). In particular, i) x-ray generator 311 radiates x-ray beam B1 toward a target object (e.g., dental arc), x-ray detector 312 receives the x-ray beam B1 at a position SP1, which penetrates the target object, and x-ray detector 312 collects data for a first x-ray image frame F1, ii) x-ray generator 311 radiates x-ray beam B2 toward a target object (e.g., dental arc), x-ray detector 312 receives the x-ray beam B1 at a position SP2, which penetrates the target object, and x-ray detector 312 collects data for a first x-ray image frame F2, and iii) x-ray generator 311 radiates x-ray beam B3 toward a target object (e.g., dental arc), x-ray detector 312 receives the x-ray beam B3 at a position SP3, which penetrates the target object, and x-ray detector 312 collects data for a third x-ray image frame F3. Such operation will be performed until collecting data for an $n^{th}$ x-ray image frame FN. After obtaining the data for a plurality of x-ray image frames, the collected data is stored in memory 330 with information on penetrating positions and directions.

Diagrams (b) and (c) illustrate reading data for a plurality of x-ray image frames and producing x-ray panoramic images including first and second panoramic images (e.g., primary panoramic image and secondary panoramic images) using the read data. In accordance with at least one embodiment, the diagram (b) illustrates a first group of x-ray image frames F1, F3, F5, . . . , Fn for reconfiguring (e.g., producing) a first x-ray panoramic image (e.g., primary panoramic image). The diagram (c) illustrates a second group of x-ray image frames F1, F2, F4, F5, F6, . . . Fn for reconfiguring (e.g., producing) at least one second x-ray panoramic image (e.g., secondary panoramic image). The embodiments of the present disclosure are not limited to the number of image frames for the first group and the second group. For example, index numbers such as F1, F2, of the image frames are randomly selected for convenience of describing and ease of understanding.

In at least one embodiment, x-ray mage frames may be selected based on a predetermined rule, as follows. For example, i) image frames for the first group may be overlapped with image frames for the second group but must be at least partially different from image frames for the second group, ii) the number of image frames for the first group is different from the number of image frames collected for the second group.

For example, when a depth resolution of a first x-ray panoramic image is lower than that of a second x-ray panoramic image, the number of x-ray image frames for the first group is fewer than the number of x-ray image frames for the second group. That is, a first image layer is a focused region of the first x-ray panoramic image, and a second image layer is a focused region of the second x-ray panoramic image. In this case, when a thickness of the first image layer is lower than a thickness of the second image layer, the number of image frames for the first group is fewer than the number of image frames for the second group.

In accordance with at least one embodiment, selection of x-ray image frames for producing a first x-ray panoramic image (e.g., primary panoramic image) and a second x-ray panoramic image (e.g., secondary panoramic image) may be differ according to properties of first and second image layers. Such selection method of data frame and the properties of first and second image layers will be described in later.

As described, the primary panoramic image and at least one secondary panoramic image are produced at step S2020 and S2030 referring back to FIG. 2. After producing the primary panoramic image and at least one secondary panoramic image may be effectively displayed together within a predetermined graphic user interface in response to a user input at steps S2040 to S2080 in accordance with at least one embodiment. Hereinafter, such a displaying operation and the predetermined graphic user interface for displaying the primary panoramic image and the secondary panoramic image will be described in more detail with reference to FIG. 5.

Figure 5:
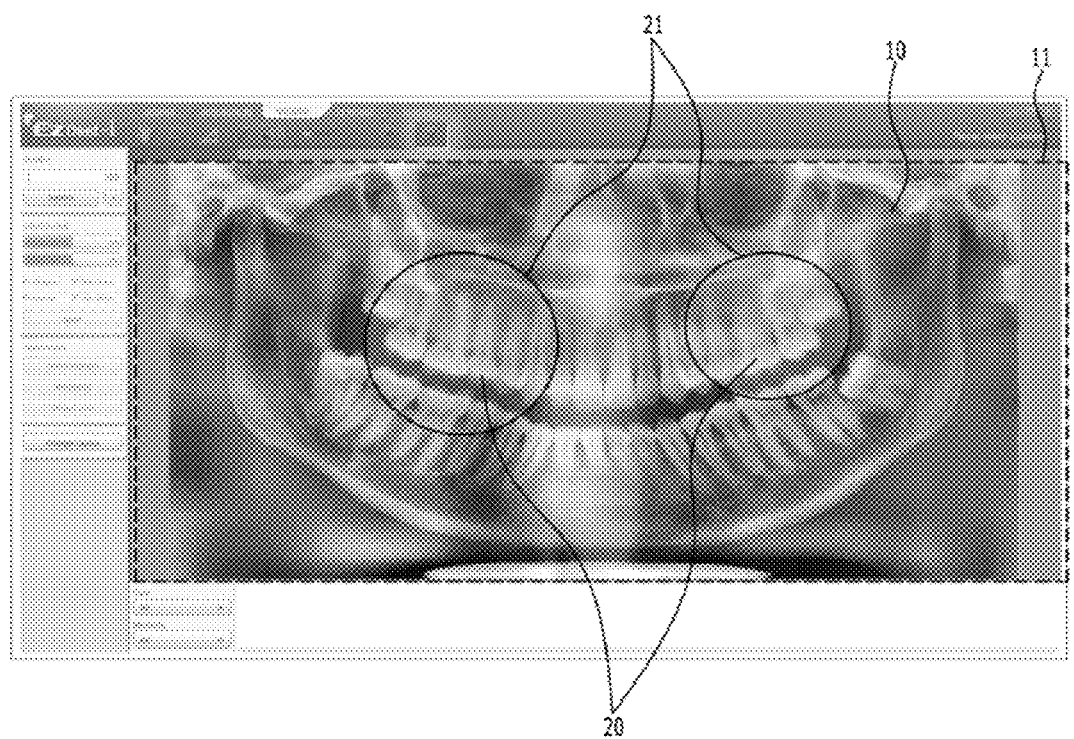
FIG. 5 illustrates a graphic user interface for effectively displaying a primary panoramic image and at least one secondary panoramic image in accordance with at least one embodiment.

FIG. 5 illustrates a graphic user interface for effectively displaying a primary panoramic image and at least one secondary panoramic image in accordance with at least one embodiment.

Referring to FIG. 5, panoramic radiography device 300 may generate graphic user interface 400 for interacting with an operator (e.g., dentist or related profession) and effectively providing panoramic images in accordance with at least one embodiment. Such generated graphic user interface 400 may be displayed on display 350.

Such graphic user interface 400 may include primary display area 11 and at least one secondary display area 21. Primary display area 11 may display primary panoramic image 10 (e.g., first panoramic image) produced based on a first image layer (e.g., a primary image layer). Secondary display area 21 may display at least part of a secondary panoramic image 20 produced based on a second image layer (e.g., secondary image layer). Here, the second image layer is entirely or partially different from the first image layer.

In FIG. 5, two secondary display areas 21 are illustrated as being positioned at predetermined regions of the primary panoramic image 10. However, the embodiments of the present disclosure are not limited thereto. For example, the number and the positions of secondary display areas 21 can be controlled in response to a user input.

In accordance with at least one embodiment, graphic user interface 400 may include more than two secondary display areas 21. For example, the number, a size, a shape, and a position of the secondary display area 21 may be controlled in response to a user input made by an input device, such as a mouse. In at least one embodiment of the present disclosure, secondary display area 21 may be provided for improving diagnosis efficiency by providing at least part of secondary panoramic image 20 having an enhanced depth resolution corresponding a selected part of primary panoramic image 10. For example, an operator (e.g., dentist) may select a part (e.g., maxillary molar) of primary panoramic image 10 to examine the part. In this case, i) secondary display area 21 may be initiated and displayed on the selected part of primary panoramic image 10, and ii) secondary display area 21 may display a correspond part (e.g., maximal molar) of secondary panoramic image 20. Such secondary panoramic image 20 may have an enhanced depth resolution for the corresponding part as compared to primary panoramic image 20.

In particular, secondary display area 21 may be initiated, created, and positioned at a predetermined region in response to a user' input (e.g., at step S2050 of FIG. 2). For example, a dentist examines a patient's dental arc based on primary panoramic image 10 displayed on primary display area 11. When the dentist wants to exam a predetermined part in primary panoramic image 10 in more detail, the dentist may select a corresponding area to exam and initiate secondary display area 21 by making a predetermined input. Then, secondary display area 21 may be overlapped on the indicated region of primary panoramic image 10. Secondary display area 21 may display a corresponding part of secondary panoramic image 20 produced by the second image layer (e.g., at step S2060 and S2070). Such secondary panoramic image 20 may have color or brightness different from that of primary panoramic image 10. Furthermore, edges of secondary display area 21 may be displayed with a bold line in order to clearly identify a boundary between secondary display area 21 and primary panoramic image 10.

In order to provide such secondary panoramic image 20, image processor 322 reconfigures and produces not only a primary panoramic image based on a first image layer but also a secondary panoramic image based on a second image layer using data for a plurality of x-ray image frames obtained during the scanning sequence operation. Hereinafter, secondary panoramic image 20 will be described as being produced based on a second image layer which includes at least one part of the first image layer or partially or entirely different from the first image layer. Herein, the scanning sequence operation may collect data for a plurality of x-ray image frames from various positions and angles while sequentially rotating radiographing member 210 along a radiographing trajectory.

In accordance with at least one embodiment, a width of x-ray detector 312 in a rotation direction may be wider than that of a typical detector. For example, the width of x-ray detector 312 is wider than about 10 mm. In general, a width of a typical x-ray detector is about 6 mm. Due to the comparatively wide x-ray detector 312, x-ray detector 312 may obtain x-ray image data within sufficient angles to improve a depth resolution of primary and secondary panoramic images.

Since a height of an x-ray sensor may be differ according to a target radiographing area or a radiographing size, it is difficult to define the height thereof. In general, a height is in a range of about 100 mm to 200 mm. A width of an x-ray sensor or a scanning sequence operation may be dynamically adjusted according to various factors. In general, x-ray detector has a width wider than 10 mm, preferably about 18 mm in accordance with at least one embodiment.

The primary panoramic image is a panoramic image produced based on at least one of first image layers. That is, the primary panoramic image may include more than two image layers overlapped to each other. The secondary panoramic image is a panoramic image produced based on at least a part of the first image layers and at least one of second image layers. At least one of the second image layers is partially or entirely different from the first image layer.

For example, when the primary panoramic image is a panoramic image produced based on a single first image layer, the second panoramic image may be i) a panoramic image produced based on a single second image layer which is different from the single first image layer associated with the first panoramic image, ii) a panoramic image produced based on the single first image layer and the single second image layer, and iii) a panoramic image produced based on the single first image layer and a plurality of second image layers.

For another example, when the first panoramic image is a panoramic image produced based on a plurality of overlapped different image layers, the second panoramic layer may be i) a panoramic image produced based on one of the first image layers of the first panoramic image, ii) a panoramic image produced based on one of the first image layers and a single second image layer, iii) a panoramic image produced at least one of the first image layers and at least one of the second image layers, and iv) a panoramic image produced more than two image layers different from the first image layers.

In accordance with at least one embodiment, the primary panoramic image may be overlapped panoramic images produced based on a plurality of first image layers in order to display comparatively wide information according to an x-ray radiation direction. The second panoramic image may be a panoramic image associated with a second image layer corresponding to at least one of the first image layers in order to enhance a depth resolution of the first panoramic image.

Herein, panoramic images produced based on respective image layers may be panoramic images with the same magnification ratio, which express a same area of a target object with a same magnification ratio in two-dimensions. The overlapped panoramic image may be a panoramic image produced based on associated multiple image layers by adding pixel values of multiple image layers, calculating an average pixel value thereof, or determining a presentative pixel value from the plurality of image layers.

In other words, the primary and secondary panoramic images may be panoramic images each having different depth resolution, which may be produced by selection and combination of panoramic images produced based on a plurality of different image layers. Such panoramic images may be selected according to a user input. Furthermore, the number, a thickness, an angle, a shape, and a position of first and second image layers for producing the primary and secondary panoramic images may be adjusted according to a user's purpose. Hereinafter, primary and secondary panoramic images will be described in more detail. For convenience of description and ease of understanding, it is assumed that each of first and second image layers is a single image layer.

An image layer for producing a panoramic image may include a focusing curved surface. Such a focusing curved surface is a focusing reference for reconfiguring or producing an associated panoramic image. Therefore, a panoramic image is projected with not only structures on the focusing curved surface of an associated image layer but also structures existing within a predetermined distance from the focusing curved surface in an x-ray radiation direction (e.g., x-ray projecting direction). For convenience, structures on the focusing curved surface are referred to as focused structures, and structures existing within a predetermined distance from the focusing curved surfaces are referred to as out-focused structures. In general, such focused structures are clearly projected on the panoramic image, and the out-focused structures are less clearly projected on the panoramic image. Accordingly, the out-focused structures in the panoramic image are blurred.

An image captured by an optical camera has a depth of a focus. For example, such a depth of a focus in the image may be shallow and deep. Like the image captured by the optical camera, an x-ray panoramic image also has a depth of a focus, and such a depth of a focus may be shallow or deep, referred to as a shallow focus or a deep focus. A relative difference between a shallow focus and a deep focus in an x-ray panoramic image is expressed as a thickness of an image layer. That is, a comparatively thin thickness of an image layer means a region in front of and in back of a focusing curved surface is comparatively thin. It also denotes a depth resolution of an associated panoramic image is comparatively high. In the accompanying drawings, a thickness of an image layer is expressed as a relative thickness. The thickness in the drawings is not an absolute thickness.

In accordance with at least one embodiment, the second image layer may have a thickness thinner than that of the first image layer. Accordingly, a depth resolution of the second panoramic image is higher than that of the first panoramic image. In order to produce such a secondary panoramic image, panoramic radiography device 300 may use x-ray image frame data obtained by radiating x-ray through each position of the second image layer within a comparatively wide angle in accordance with at least one embodiment.

In accordance with another embodiment, the first and second image layers may be controlled to have a thickness comparatively thinner than a typical image layer in order to improve the depth resolution of the first and second panoramic images. Such a method of enhancing a depth resolution of primary and secondary panoramic images by controlling a thickness of the first and/or second image layer will be described with reference to FIG. 12 in later.

As described, primary panoramic image 10 and secondary panoramic image 20 may be produced based on at least one first image layer and at least one second image layer, respectively in accordance with at least one embodiment. Hereinafter, such first and second image layers for producing primary panoramic image 10 and secondary panoramic image 20 will be described in more detail.

Figure 6:
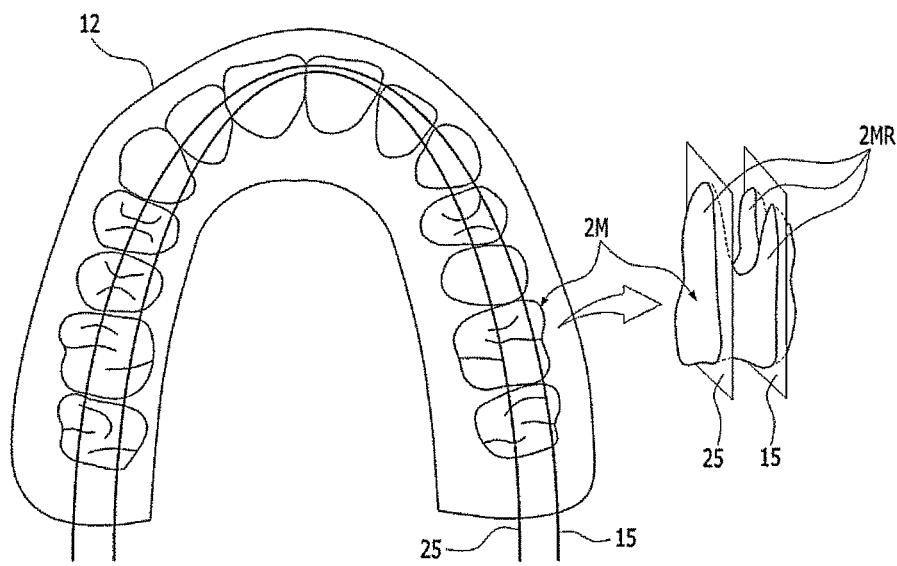
FIG. 6 illustrates first and second image layers for producing primary and secondary panoramic images in accordance with at least one embodiment.

FIG. 6 illustrates first and second image layers for producing primary and secondary panoramic images in accordance with at least one embodiment.

Referring to FIG. 6, panoramic radiography device 300 may radiograph upper jaw 12 (e.g., maxilla), produce, and provide primary panoramic image 10 and secondary panoramic image 20 (shown in FIG. 5). That is, primary panoramic image 10 of FIG. 5 may be produced using first image layer 15, and secondary panoramic image 20 of FIG. 5 may be produced using second image layer 25. The number, the angle, the shape, and the position of the first and second image layers are schematically and exemplary illustrated in FIG. 5 for convenience of description and ease of understanding. Therefore, embodiments of the present disclosure are not limited thereto.

In accordance with at least one embodiment, at least one of the number, the angle, the shape, and the position of the first image layer 15 is different from those of the second image layer 25. The shape of an image layer denotes an overall shape of the image layer which is shaped according to a curvature of various parts forming the image layer.

For example, two panoramic images including second maxillary molar 2M may be produced using first and second image layers passing through the second maxillary molar 2M. As shown, the second maxillary molar 2M has an outer side close to rips of a patient and an inner side close to a tongue. The outer side of the second maxillary molar 2M has two roots 2MR-2, and the inner side of the second maxillary molar 2M has one root 2MR-1. As shown in FIG. 6, the first image layer 15 passes through the two roots 2MR-2, and the second image layer 25 passes through the one root 2MR-1. Accordingly, when primary panoramic image 10 is produced by focusing first image layer 15, the primary panoramic image 10 includes an image of two roots 2MR-2, but not one root 2MR-1. When secondary panoramic image 20 is produced by focusing second image layer 25, the secondary panoramic image 20 includes an image of one root 2MR-1, but not two roots 2MR-2. As described, the secondary panoramic image 20 produced based on the second image layer 25 may provide panoramic image information different from the primary panoramic image 10. The panoramic image information may be information on a number, an angle, a shape, and a position.

In FIG. 6, each of first and second image layers 15 and 25 is illustrated as a single image layer. However, the embodiments of the present disclosure are not limited thereto. That is, in another embodiment of the present invention, a plurality of image layers may be provided as first image layers 15 or second image layers 25. In this case, the plurality of image layers may be different in at least one of the number, a shape, a position, and angle. Furthermore, according to a user's input, at least one of the number, the shape, the position, and the angle of first and second image layers 15 and 25 may be dynamically changed. For example, a user may make a selection through a viewer module. Such a viewer module may display a control menu for enabling a user to make selection and display a secondary panoramic image according to the user selection made through the view module.

Figure 7:
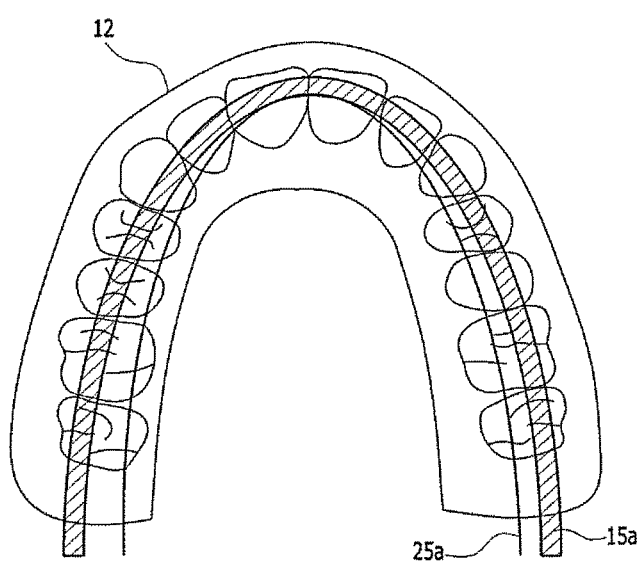
FIG. 7 illustrates first and second image layers for producing primary and secondary panoramic images in accordance with another embodiment.

FIG. 7 illustrates first and second image layers for producing primary and secondary panoramic images in accordance with another embodiment.

Referring to FIG. 7, first image layer 15a may be comparatively thicker than second image layer 25a. Accordingly, primary panoramic image 10 may contain information on more structures in comparatively wide areas in an x-ray radiation direction. That is, comparatively more information is overlapped in primary panoramic image 10 as compared to an image layer has a comparatively thinner thickness. As described, the first image layer 15a and the second image layer 25a may be different in a thickness as well as the number, an angle, a shape, and a position. The second image layer 25a may be partially or entirely overlapped with the first image layer 15a. Furthermore, the second image layer 25a may be completely different from the first image layer 15a.

In FIG. 7, each of first and second image layers 15a and 25a is illustrated as a single image layer. However, the embodiments of the present disclosure are not limited thereto. That is, in another embodiment of the present invention, a plurality of image layers may be provided as first image layers 15 or second image layers 25. In this case, the plurality of image layers may be different in at least one of the number, a shape, a position, an angle, and a thickness. Furthermore, according to a user's input, at least one of the number, the shape, the position, the angle, and the thickness of first and second image layers 15a and 25a may be dynamically changed.

Figure 8:
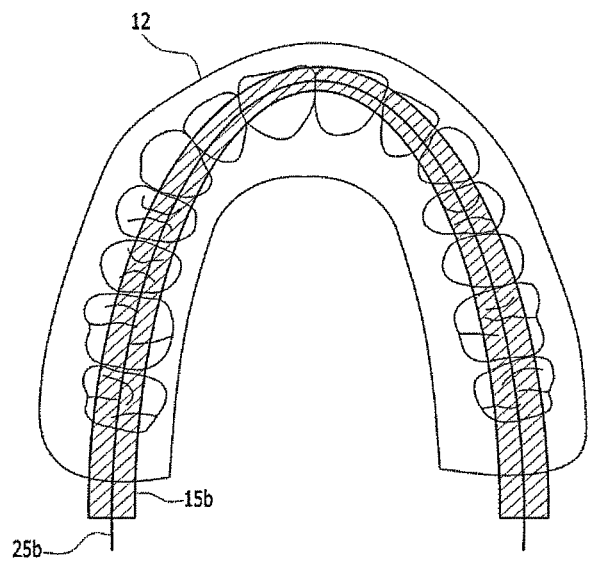
FIG. 8 illustrates first and second image layers for producing first and second panoramic images in accordance with still another embodiment.

FIG. 8 illustrates first and second image layers for producing first and second panoramic images in accordance with still another embodiment.

Referring to FIG. 8, first image layer 15b and second image layer 25b may be entirely overlapped, and the first image layer 15b may have a thickness comparatively thicker than the second image layer 25b. For example, the first image layer 15b for the primary panoramic image may be set to have a thickness covering entire thickness of teeth arranged along a dental arc, and the second image layer 25b may be set to have a thickness thinner than the first image layer 15b. In this case, the secondary panoramic image may be produced with enhanced depth resolution. That is, the second panoramic image may have a sharper image than the first panoramic image.

In embodiments shown in FIG. 7 and FIG. 8, the primary panoramic image maybe produced using one thick image layer or a plurality of thin image layers. In case of using the plurality of thin image layers, the plurality of thin image layers may be overlapped and used as one thick image layer for producing a corresponding panoramic image. In this case, the secondary panoramic image may be one of a plurality of panoramic images overlapped for producing the primary panoramic image. A panoramic image of each image layer may have the same magnificent ratio. That is, the primary and secondary panoramic images have the same magnificent ratio.

In accordance with at least one embodiment, a thickness of an image layer may be dynamically controlled in order to control a depth resolution of a panoramic image. Such features of controlling a depth resolution of a panoramic image by controlling a thickness of an image layer will be described with reference to FIG. 12.

In accordance with at least one embodiment, a shape and a position of a second image layer 25b may be set to include a part of a target object (e.g., dental arc, teeth) frequently photographed for diagnosis. Accordingly, it is possible to improve user's convenience and to reduce a radiation exposure amount to a patient. The number of image layers is not limited to one. Such parameters may be controlled dynamically in response to a user's input.

Figure 9:
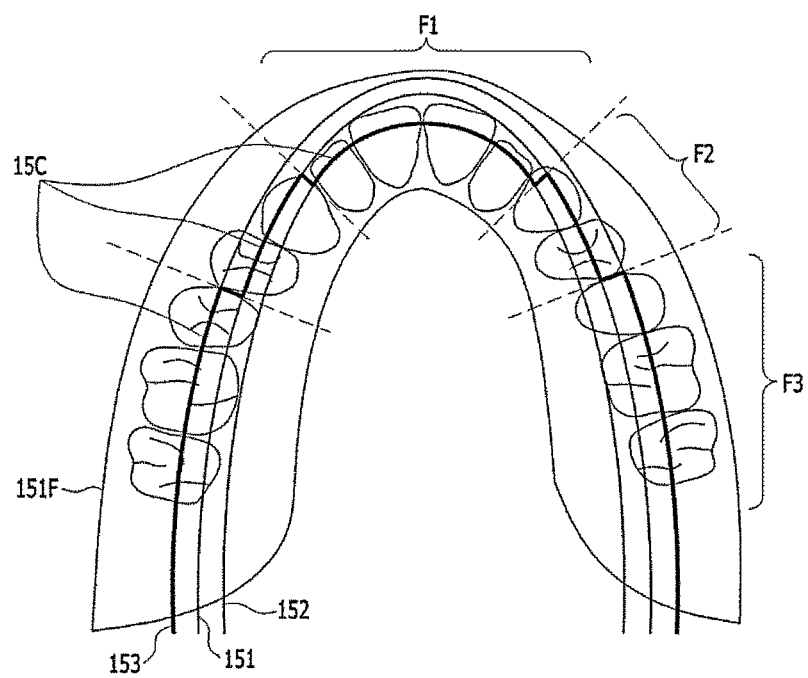
FIG. 9 illustrates first image layers used for producing a primary panoramic image in accordance with at least one embodiment.

FIG. 9 illustrates first image layers used for producing a primary panoramic image in accordance with at least one embodiment.

Referring to FIG. 9, a primary panoramic image may be a panoramic image auto focused through a multi-layer method in accordance with at least one embodiment. For example, multiple image layers 151, 152, and 153 may be used to produce the auto focused primary panoramic image. Such multiple image layers 151, 152, and 153 may be divided into image layer parts by each section F1, F2, F3. Then, at each section F1, F2, F3, one image layer part having a referenced surface matched with a corresponding image layer is selected from three image layers 151, 152, and 153. For example, i) an image layer part of layer 152 is selected in the section F1, ii) an image layer part of layer 151 is selected in the section F2, and iii) an image layer part of layer 153 is selected. Then, the first image layer may be formed by combining the selected image layer parts.

For another example, three panoramic images may be reconfigured and produced based on three image layers 151, 152, and 153. The produced three panoramic images may be divided into multiple panoramic image parts by each section F1, F2, and F3. Then, at each section F1, F2, F3, one panoramic image part having clearest image is selected from three panoramic images. Then, the primary panoramic image may be produced by combining the selected panoramic image parts.

The above methods are described in U.S. patent application Ser. No. 12/863,181 and U.S. patent application Ser. No. 13/509,042, which are filled by a common applicant. The subject matter of this application is related to U.S. patent application Ser. No. 12/863,181 and U.S. patent application Ser. No. 13/509,042, the teaching of which are incorporated herein their entirety by reference.

Figure 10:
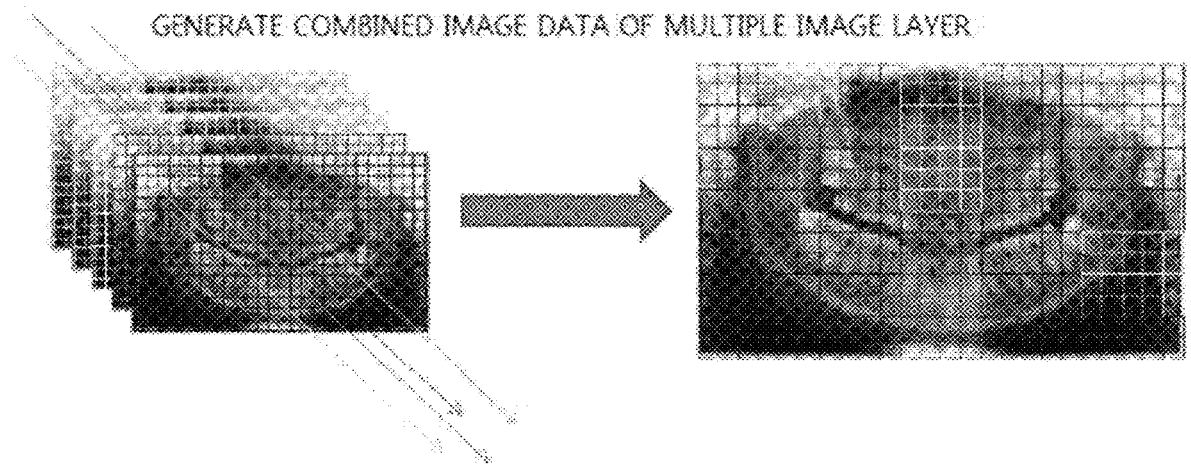
FIG. 10 illustrates a primary panoramic image in accordance with another embodiment.

FIG. 10 illustrates a primary panoramic image in accordance with another embodiment.

Referring to FIG. 10, the primary panoramic image may be produced by i) dividing a) panoramic images produced based on a plurality of image layers or b) image data of a plurality of image layers by a unit block, ii) comparing related image blocks and selecting one having the clearest image from the related image blocks, and iii) combining the selected image blocks.

The above methods are described in U.S. patent application Ser. No. 12/863,181, U.S. patent application Ser. No. 14/401,726, and U.S. patent application Ser. No. 14/401,716, which are filled by a common applicant. The subject matter of this application is related to U.S. patent application Ser. No. 12/863,181, U.S. patent application Ser. No. 14/401,726, and U.S. patent application Ser. No. 14/401,716, the teaching of which are incorporated herein their entirety by reference.

Figure 11:
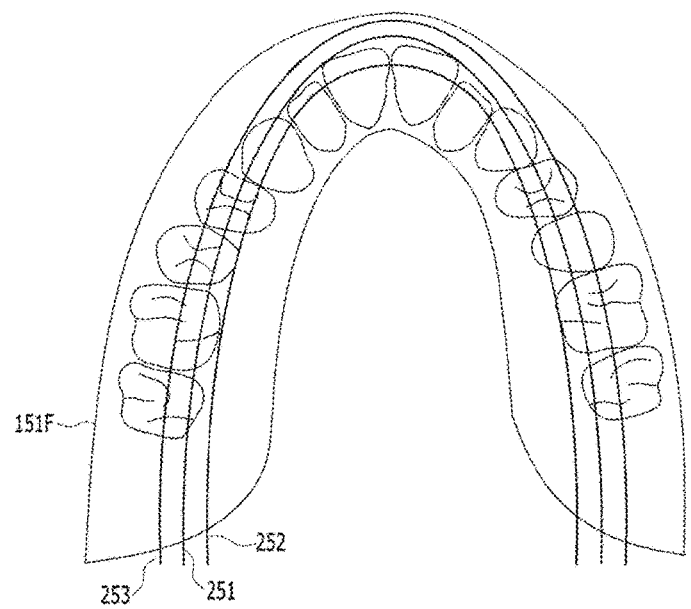
FIG. 11 illustrates a second image layer for producing a secondary panoramic image in accordance with at least one embodiment.

FIG. 11 illustrates a second image layer for producing a secondary panoramic image in accordance with at least one embodiment.

Referring to FIG. 11, a secondary panoramic image may be produced using a plurality of second image layers 251, 252, and 253. Such second image layers 251, 252, and 253 may be previously set and stored in panoramic radiography device 300. For example, a plurality of second image layers 251, 252, and 253 may include a central image layer passing a center of a dental arc, an outer image layer passing an outer side of the dental arc, and an inner image layer passing an inner side of the dental arc. Furthermore, such second image layers may be set not to cross each other.

Figure 12:
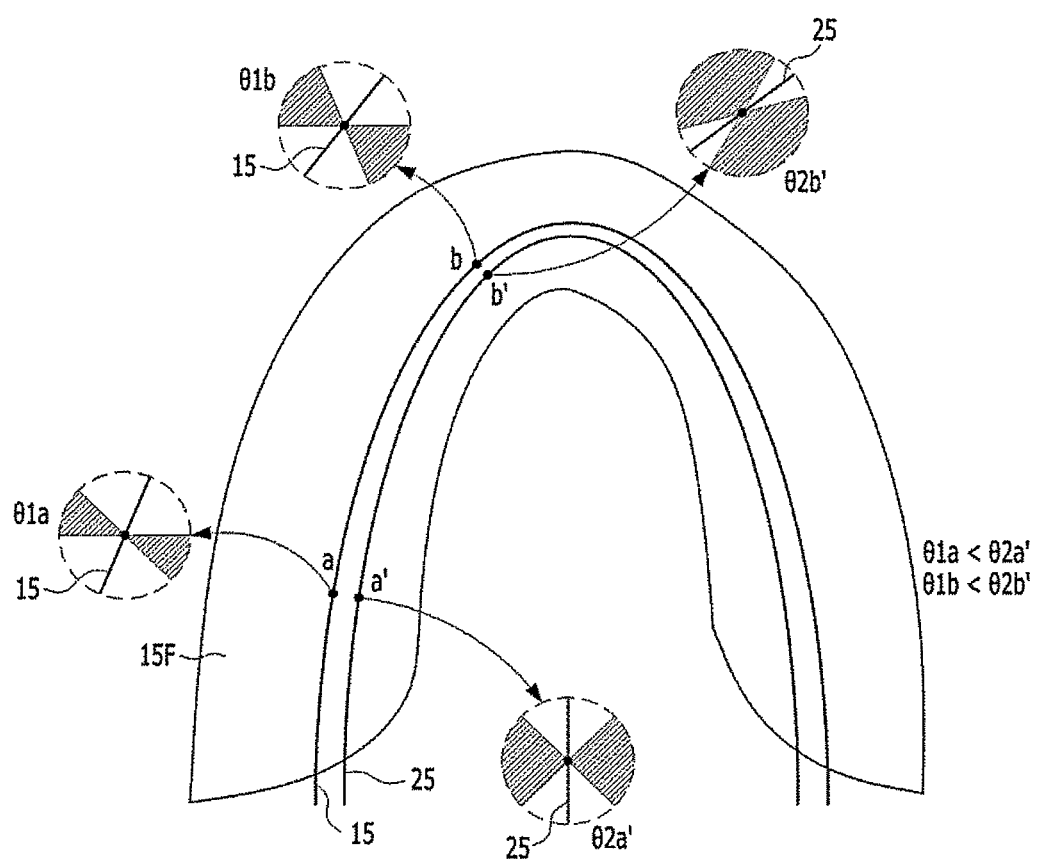
FIG. 12 illustrates a range of x-ray image frame data used for reconfiguring panoramic images in accordance with at least one embodiment.

FIG. 12 illustrates a range of x-ray image frame data used for reconfiguring panoramic images in accordance with at least one embodiment.

As described, panoramic radiography device 300 may i) perform a scanning sequence operation for obtaining data of a plurality of x-ray image frames (e.g., referred to as "x-ray image frame data"), ii) store the obtained x-ray image frame data in a memory, iii) reads necessary x-ray image frame data for reconfiguring (e.g., producing) panoramic images from the memory, iv) produce panoramic images based on the read x-ray image data using a direct back projection (DBP) method in accordance with at least one embodiment. The necessary x-ray image frame data for producing a panoramic image using a predetermined image layer may be x-ray image data included within a predetermined angle range formed by at least two x-ray beams passing through the predetermined image layer. For example, such a predetermined angle range is shown as $\theta 1a$, $\theta 1b$, $\theta 2a'$, and $\theta 2b'$. That is, x-ray image frame data included in angle ranges $\theta 1a$, $\theta 1b$, $\theta 2a'$, and $\theta 2b'$ may be used to produce a panoramic image. Furthermore, if necessary, a part of the necessary x-ray image frame data may be calculated through interpolation. For convenience, such a predetermined angle range is referred to as an x-ray incident angle range hereinafter.

A depth resolution of a panoramic image may be changed according to such an x-ray incident angle range. In particular, if x-ray image frame data associated with a predetermined x-ray incident angle are used to produce a panoramic image, all structures present along a corresponding x-ray radiation path are overlapped to one plane. That is, the produced panoramic image may have no depth resolution. However, if x-ray image frame data present in a predetermined x-ray incident angle range are used to produce a panoramic image, the produced panoramic image may have an enhanced depth resolution. That is, a panoramic image with a comparatively thin image layer may be produced using image frame data within an x-ray incident angle range. That is, the wider the x-ray incident angle range is, the better the depth resolution becomes.

In accordance with at least one embodiment, panoramic radiography device 300 may produce a primary panoramic image (e.g., first panoramic image) using x-ray image frame data within a predetermined x-ray incident angle range at each position of the first image layer 15. For example, x-ray image frame data within a predetermined x-ray incident angle range $\theta 1a$ may be used at a position "a" of the first image layer 15, and x-ray image frame data within a predetermined x-ray incident angle range $\theta 1b$ may be used at a position "b" of the first image layer 15.

Furthermore, panoramic radiography device 300 may produce a secondary panoramic image (e.g., second panoramic image) using x-ray image frame data within a predetermined x-ray incident angle range at each position of the second image layer 25. For example, x-ray image frame data within a predetermined x-ray incident angle range $\theta 2a'$ may be used at a position "a'" of the second image layer 25, and x-ray image frame data within a predetermined x-ray incident angle range $\theta 2b'$ may be used at a position "b'" of the second image layer 25.

The position "a'" of second image layer 25 may be a corresponding position of the position "a" of first image layer 15. That is, a normal line crossing the position "a" of first image layer 15 also crosses the position "a'" of second image layer 25. The normal line is along an x-ray radiation direction. The position "b'" of second image layer 25 may be a corresponding position of the position "b" of first image layer. That is, a normal line crossing the position "b" of first image layer 15 also crosses the position "b'" of second image layer 25. Furthermore, x-ray incident angle ranges $\theta 1a$, $\theta 1b$, $\theta 2a'$, and $\theta 2b'$ have following relations: $\theta 1a < \theta 2a'$, and $\theta 1b < \theta 2b'$. By setting such conditions for the x-ray incident angle ranges, second image layer 25 has comparatively superior depth resolution than first image layer 15. That is, a thickness of second image layer 25 is thinner than that of first image layer 15.

As described, panoramic radiograph device 300 in accordance with at least one embodiment may i) obtain x-ray image frame data within a predetermined x-ray incident angle range of each position at a corresponding image layer and ii) produce panoramic images based on the obtained x-ray image frame data using a direct back projection (DBP) method. Panoramic radiography device 300 may enable a user to select an image layer, the number of image layers, an angle, a position, and a shape thereof. Furthermore, panoramic radiography device 300 may enable a user to select a thickness of an image layer and a x-ray incident angle range. Accordingly, a user may control a depth resolution of at least one of primary and secondary panoramic images.

Figure 13:
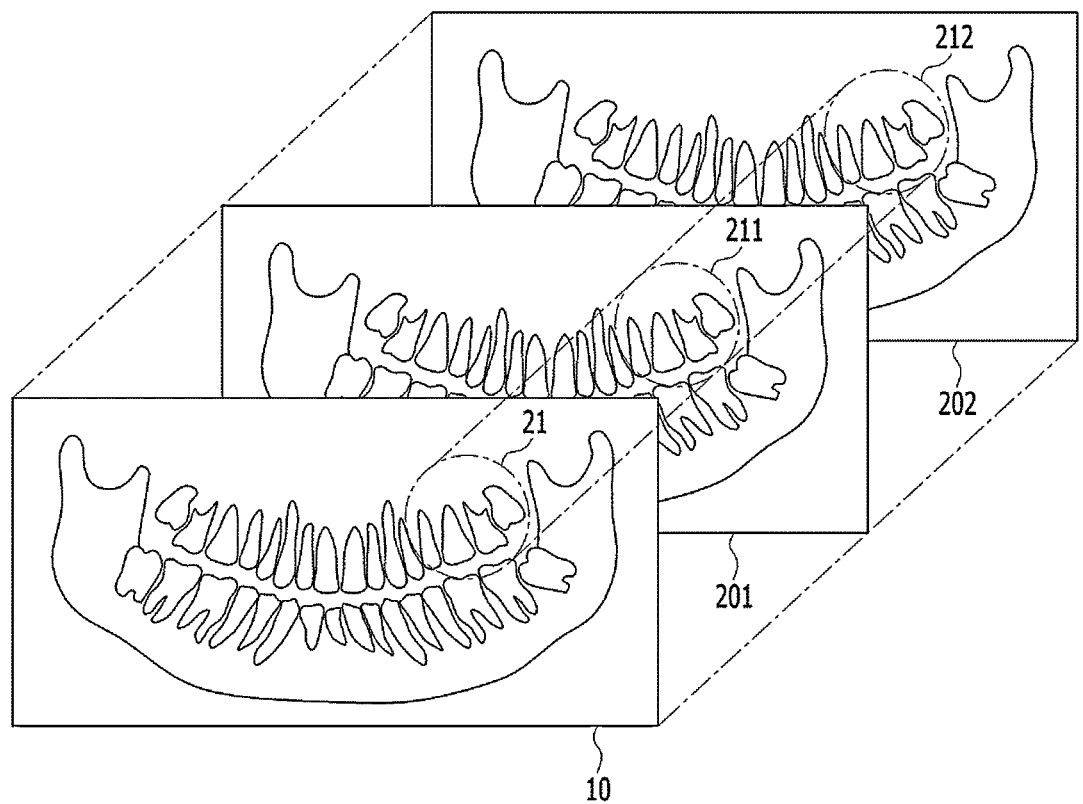
FIG. 13 illustrates arrangement of a primary panoramic image and secondary panoramic images in accordance with at least one embodiment.

FIG. 13 illustrates arrangement of a primary panoramic image and secondary panoramic images in accordance with at least one embodiment.

For convenience of description and ease of understanding, a single primary panoramic image and two secondary panoramic images are illustrated. However, embodiments of the present disclosure are not limited thereto.

As shown in FIG. 13, secondary panoramic images 201 and 202 are panoramic images expressing a same range of a target object with identical magnification and identical frame size, as compared to primary panoramic image 10. For example, such secondary panoramic images 201 and 202 may be produced when related primary panoramic 10 at steps S2020 and S2030. Furthermore, such secondary panoramic images 201 and 202 may be stored after producing at step S2030. At least one of indicated parts 211 and 212 of secondary panoramic images 210 and 202 may be produced by viewer module 323 and displayed through secondary display areas 21 of graphic user interface shown in FIG. 5.

Figure 14:
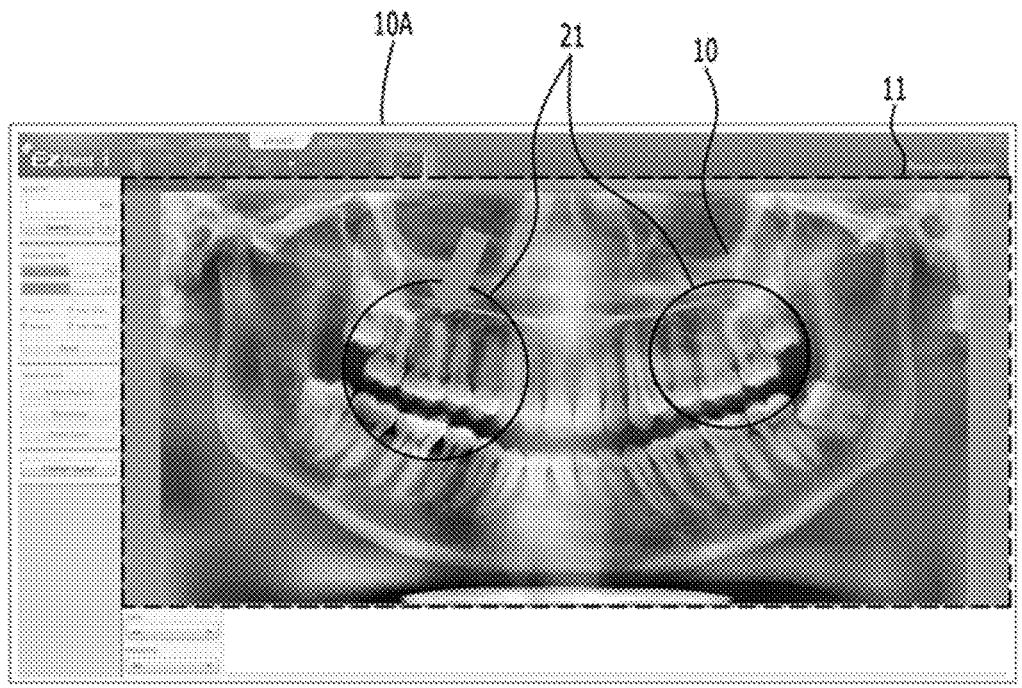
FIG. 14 is a diagram for comparing a primary panoramic image and secondary panoramic images in accordance with at least one embodiment.
Figure 14:
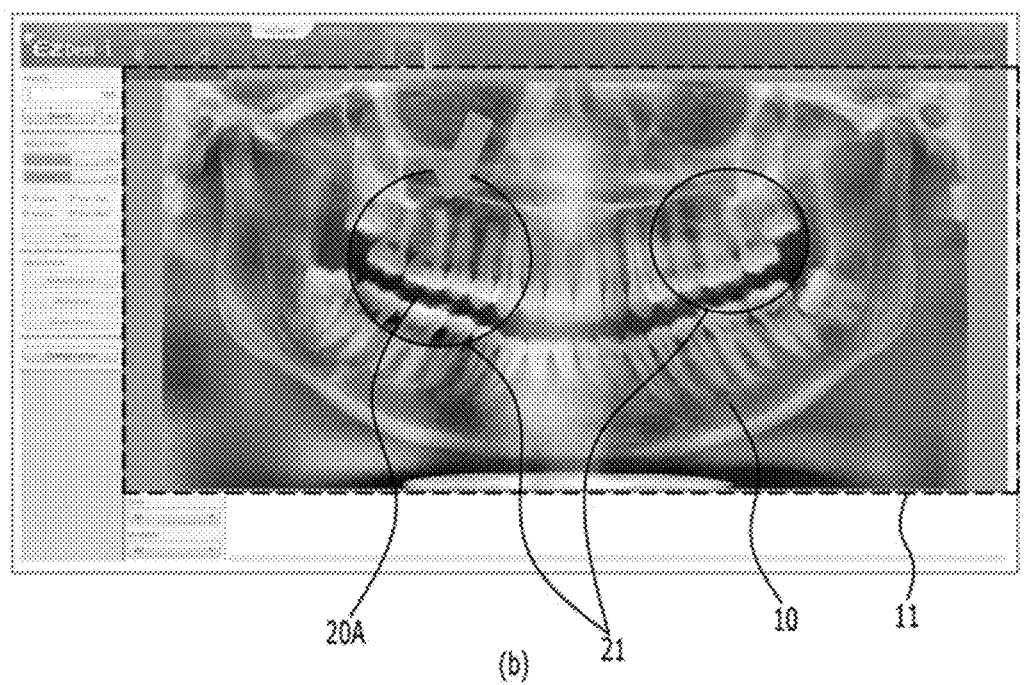

FIG. 14 is a diagram for comparing a primary panoramic image and secondary panoramic images in accordance with at least one embodiment.

Referring to FIG. 14, two graphic user interfaces in diagrams (a) and (b) display same primary panoramic image 10 in primary display area 11. However, graphic user interfaces in diagram (a) and (b) display different secondary panoramic images through secondary display areas 21 indicated by an arrow line.

In particular, in diagram (a), secondary display area 21 displays a secondary panoramic image showing a single root of a maxillary molar. In diagram (b), secondary display area 21 displays another secondary panoramic image showing two roots of the same maxillary molar.

As described, in accordance with at least one embodiment, a user may be enabled to initiate and display the secondary display area 21 by selecting a desired position on the graphic user interface through making an input using a mouse and to select one of secondary panoramic images (e.g., 201 and 202) by turning a wheel of the mouse (for example at step S2050 to S2080 of FIG. 2).

Figure 15:
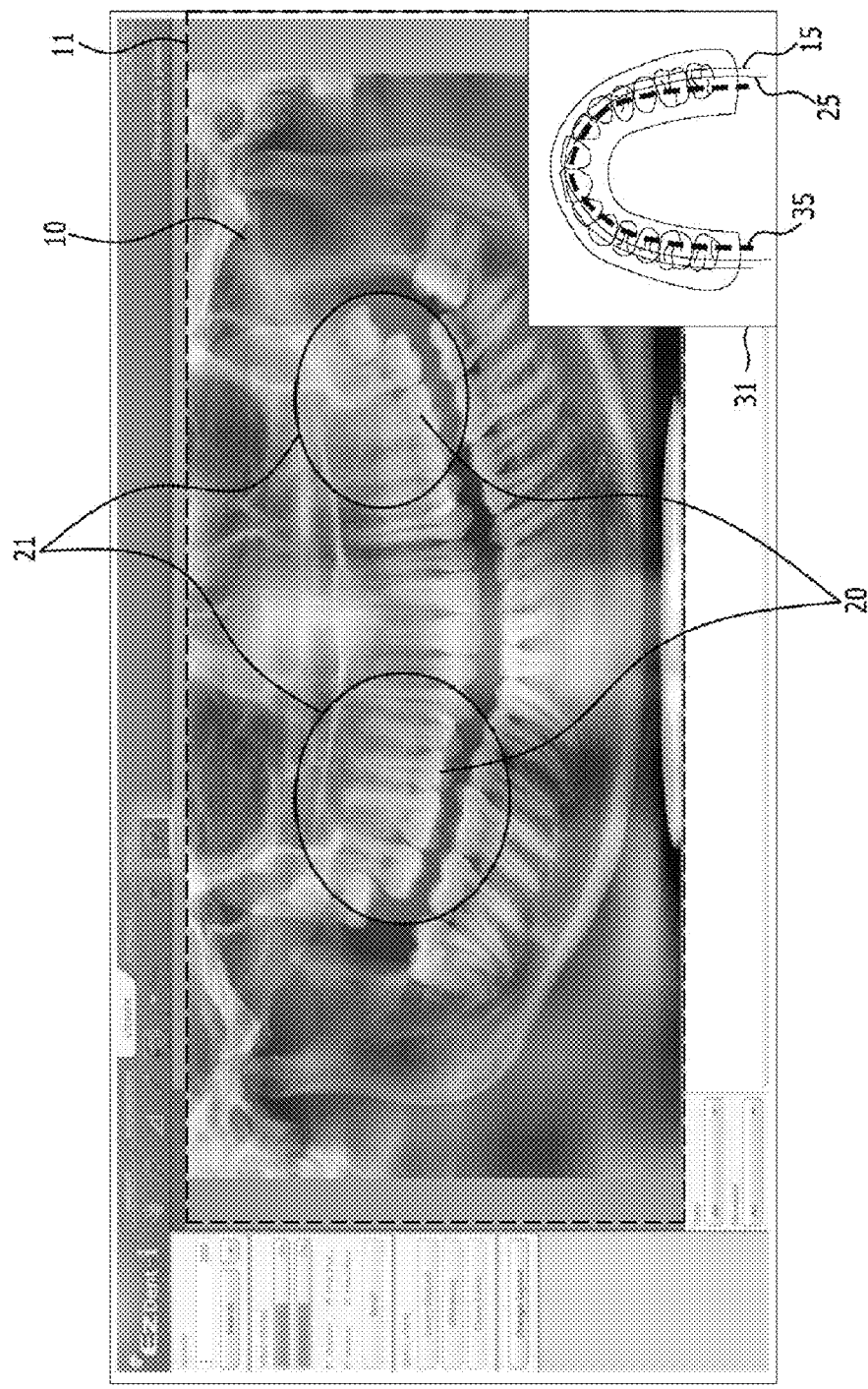
FIG. 15 illustrates a graphic user interface provided by a panoramic radiography device in accordance with another embodiment of the present invention.

FIG. 15 illustrates a graphic user interface provided by a panoramic radiography device in accordance with another embodiment of the present invention.

Referring FIG. 15, the graphic user interface may further include image layer indictor 31 for indicating an image layer associated with a secondary panoramic image 20 which is displayed through secondary display area 21. Such an image layer indicator 31 may display a first image layer 15 associated with a primary panoramic image 10, a second image layer 25 associated with a second panoramic image 20, the number, a thickness, an angle, a shape, and a position thereof using at least one of numeral references, drawings, symbols, and likes. Through the image layer indicator 31, a user can intuitively recognize relation between first and second image layers and corresponding panoramic images.

As described, panoramic radiography device 300 may simultaneously display i) a primary panoramic image produced using at least one first image layer and ii) at least one part of secondary panoramic images produced using at least one second image layer partially or entirely different from the first image layer through a graphic user interface in accordance with at least one embodiment.

FIG. 16 to FIG. 20 are graphic user interfaces of a panoramic radiography device for describing operations thereof in accordance with at least one embodiment.

Figure 16:
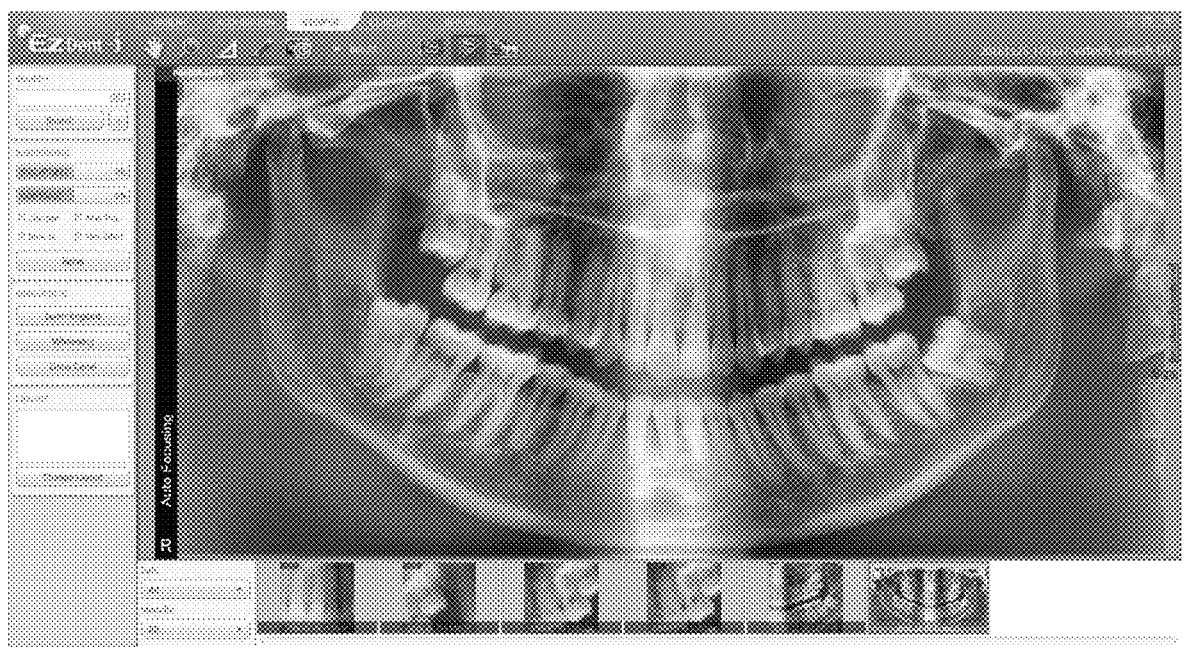
FIG. 16 to FIG. 20 are graphic user interfaces of a panoramic radiography device for describing operations thereof in accordance with at least one embodiment.

As shown in FIG. 16, a viewer module may i) produce a graphic user interface and a primary panoramic image and ii) display the graphic user interface with the primary panoramic image on a primary display area. The primary panoramic image may be a panoramic image produced using a plurality of image layers with the same magnification. In another embodiment, the primary panoramic image may be produced by an image processor, or the image processor in cooperation with the viewer module. Such operations may be performed in steps S2020 and S2030 in FIG. 2.

Figure 17:
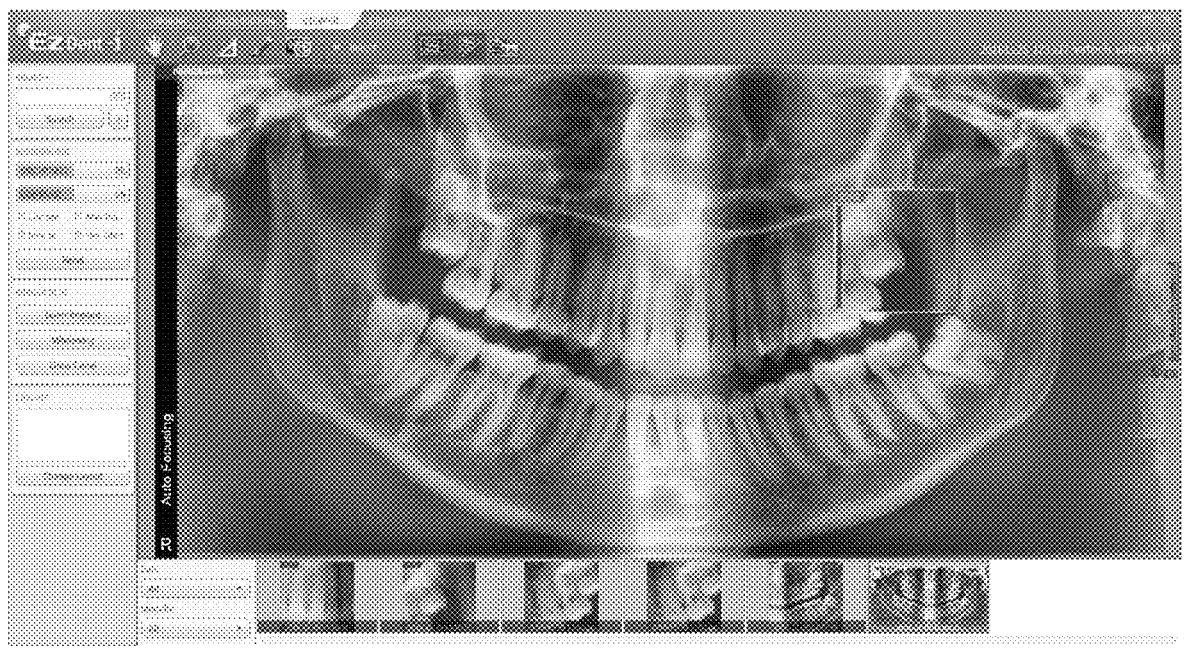

As shown in FIG. 17, a user may initiate a secondary display area at an indicated part of the primary panoramic image by selecting the indicated part using an input unit. The secondary display area may be displayed at the indicated part and display a corresponding part of a secondary panoramic image, which is corresponding to an indicated part of the primary panoramic image. Such operations may be performed in steps S2050 to S2080.

Figure 18:
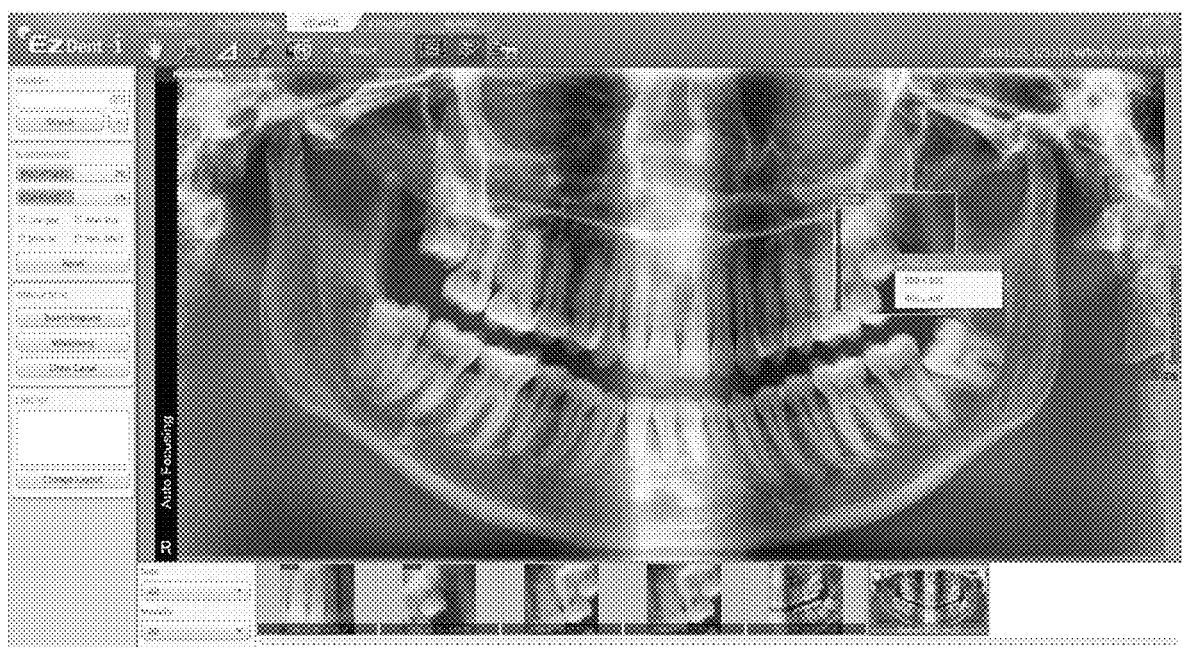

As shown in FIG. 18, the secondary display area may display a corresponding part of a secondary panoramic image in real time. Furthermore, the user may be allowed to control the secondary display area, such as move and resize of the secondary display area or to select one of secondary panoramic images to display. Such operations may be performed in steps S2050 to S2080.

The secondary panoramic image may be a panoramic image produced using one of image layers used to produce the primary panoramic image. In this case, a predetermined indicator may be displayed with the secondary display area to indicate the currently used secondary panoramic image among a plurality of secondary panoramic images. For example, when the indicator displays "20/40", it means the $20^{th}$ secondary panoramic image is displayed among 40 secondary panoramic images.

Figure 19:
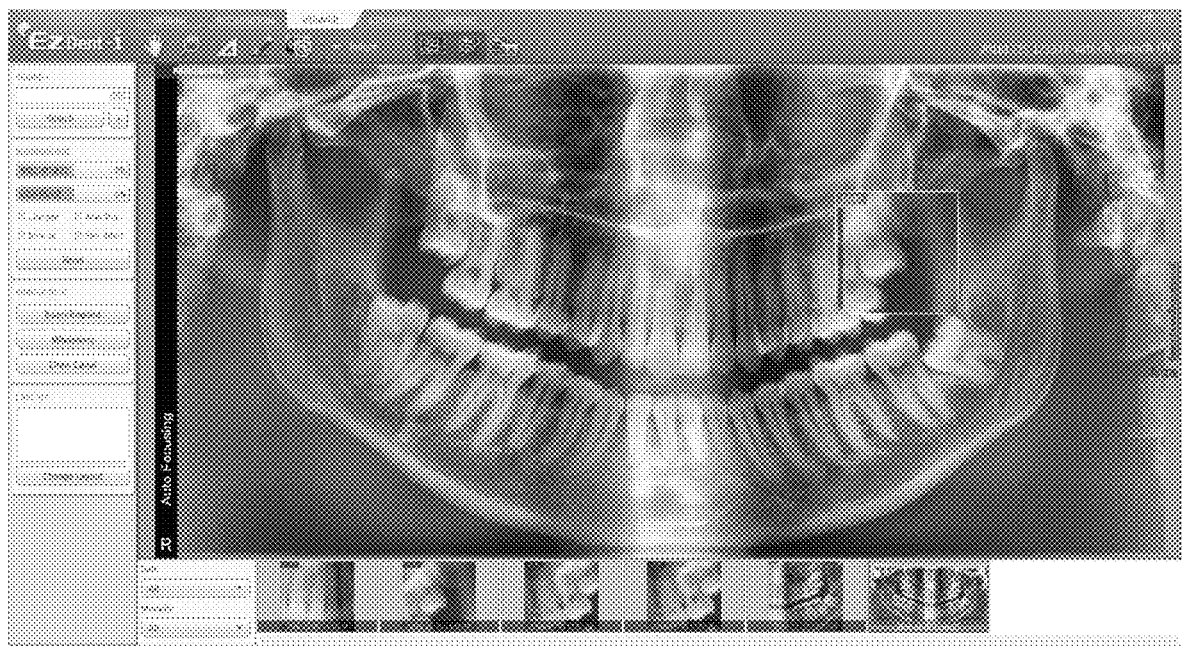

As shown in FIG. 19, a user may be allowed to select one of secondary panoramic images. For example, the user can select one (e.g., $14^{th}$) among 40 secondary panoramic images by turning a wheel of the mouse. The indicator of FIG. 19 shows that the current secondary panoramic image displayed in the secondary display area is the $14^{th}$ secondary panoramic image.

Figure 20:
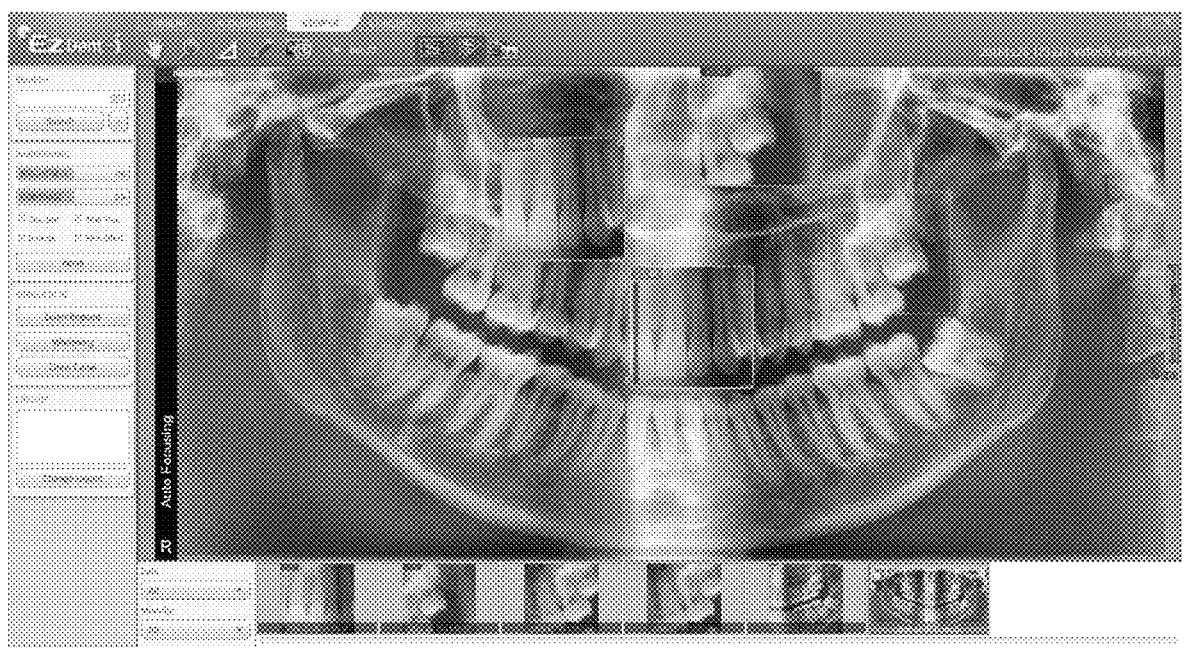

As shown in FIG. 20, a part of a secondary panoramic image displayed in a secondary display area may be captured and provided. For example, a captured image may be displayed with a related part of a secondary panoramic image. Such a captured image may be stored in a memory as an image file. In particular, the viewer module may provide options with the graphic user interface in order to enable a user to capture a predetermined part of images (e.g., primary panoramic image and second panoramic images), to store the captured image, and to display the captured image at a predetermined position within the graphic user interface.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, the terms "system," "component," "module," "interface,", "model" or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

The present invention can be embodied in the form of methods and apparatuses for practicing those methods. The present invention can also be embodied in the form of program code embodied in tangible media, non-transitory media, such as magnetic recording media, optical recording media, solid state memory, floppy diskettes, CD-ROMs, hard drives, or any other machine-readable storage medium, wherein, when the program code is loaded into and executed by a machine, such as a computer, the machine becomes an apparatus for practicing the invention. The present invention can also be embodied in the form of program code, for example, whether stored in a storage medium, loaded into and/or executed by a machine, or transmitted over some transmission medium or carrier, such as over electrical wiring or cabling, through fiber optics, or via electromagnetic radiation, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits. The present invention can also be embodied in the form of a bitstream or other sequence of signal values electrically or optically transmitted through a medium, stored magnetic-field variations in a magnetic recording medium, etc., generated using a method and/or an apparatus of the present invention.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

As used herein in reference to an element and a standard, the term "compatible" means that the element communicates with other elements in a manner wholly or partially specified by the standard, and would be recognized by other elements as sufficiently capable of communicating with the other elements in the manner specified by the standard. The compatible element does not need to operate internally in a manner specified by the standard.

No claim element herein is to be construed under the provisions of 35 U.S.C. § 112, sixth paragraph, unless the element is expressly recited using the phrase "means for" or "step for."

Although embodiments of the present invention have been described herein, it should be understood that the foregoing embodiments and advantages are merely examples and are not to be construed as limiting the present invention or the scope of the claims. Numerous other modifications and embodiments can be devised by those skilled in the art that will fall within the spirit and scope of the principles of this disclosure, and the present teaching can also be readily applied to other types of apparatuses. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A panoramic radiography device comprising:
   a processor configured to produce a plurality of x-ray panoramic images of a target object using a plurality of x-ray image frame data, wherein each of the x-ray panoramic images is produced based on a corresponding image layer that is a focusing layer of the target object, and image layers of the plurality of x-ray panoramic images are sequentially arranged along an x-ray radiation direction;
   a memory configured to store the plurality of panoramic images of the target object;
   an input unit configured to receive an input from an operator; and
   a viewer module configured to provide a graphic user interface,
   display a first panoramic image, which is produced using one of the plurality of image layers, on the graphic user interface, and replace a partial region of the first panoramic image with a corresponding part of a second panoramic image, which is produced using another one pointed by the input among the plurality of image layers while displaying the first panoramic image;
   wherein the plurality of panoramic images stored in the memory have the same magnification,
   wherein in an event that the input unit receives a series of inputs consecutively pointing different image layers of the second panoramic image in the x-ray radiation direction, the viewer module continuously changes the corresponding part of second panoramic image, with corresponding parts of panoramic images produced by image layers consecutively pointed by the series of inputs.

2. The panoramic radiography device of claim 1, wherein the viewer module is configured to display a relative position of the image layer of the second panoramic image with respect to the image layer of the first panoramic image by at least one of a number and a figure.

3. The panoramic radiography device of claim 1, wherein the viewer module is configured to change at least one of a position, a size, a shape, and a number of the partial region response to the input.

* * * * *